United States Patent
Safran et al.

(10) Patent No.: US 9,576,107 B2
(45) Date of Patent: Feb. 21, 2017

(54) MODEL BASED RECONSTRUCTION OF THE HEART FROM SPARSE SAMPLES

(71) Applicant: BIOSENSE WEBSTER (ISRAEL) LTD.

(72) Inventors: Moshe Safran, Rehovot (IL); Meir Bar-Tal, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

(21) Appl. No.: 14/313,214

(22) Filed: Jun. 24, 2014

(65) Prior Publication Data

US 2015/0018698 A1    Jan. 15, 2015

Related U.S. Application Data

(60) Provisional application No. 61/844,024, filed on Jul. 9, 2013.

(51) Int. Cl.
*G06F 19/00*        (2011.01)
*G06F 17/11*        (2006.01)
*A61B 5/053*        (2006.01)

(52) U.S. Cl.
CPC ......... *G06F 19/3437* (2013.01); *A61B 5/0538* (2013.01); *G06F 17/11* (2013.01)

(58) Field of Classification Search
CPC ..... G06F 19/3437; A61B 5/05; A61B 5/0538; A61B 5/0033; A61B 5/103; A61B 5/107
USPC ............................ 345/420; 600/508; 128/898
See application file for complete search history.

(56) References Cited

U.S. PATENT DOCUMENTS

| | | | |
|---|---|---|---|
| 5,307,807 A * | 5/1994 | Valdes Sosa et al. | 600/409 |
| 5,315,537 A * | 5/1994 | Blacker | 716/51 |
| 5,687,737 A * | 11/1997 | Branham | A61B 5/0422 600/509 |
| 5,889,524 A * | 3/1999 | Sheehan et al. | 345/419 |
| 6,226,542 B1 | 5/2001 | Reisfeld | |
| 6,226,543 B1 | 5/2001 | Gilboa | |
| 6,301,496 B1 | 10/2001 | Reisfeld | |
| 6,814,733 B2 | 11/2004 | Schwartz | |
| 6,892,091 B1 | 5/2005 | Ben Haim | |
| 6,950,689 B1 | 9/2005 | Willis | |
| 6,997,924 B2 | 2/2006 | Schwartz | |
| 7,155,042 B1 | 12/2006 | Cowan | |
| 7,156,816 B2 | 1/2007 | Schwartz | |
| 7,184,820 B2 * | 2/2007 | Jersey-Willuhn et al. | 600/547 |
| 7,242,793 B2 | 7/2007 | Trobaugh | |
| 7,327,872 B2 | 2/2008 | Vaillant | |
| 7,440,609 B2 | 10/2008 | Von Berg | |

(Continued)

OTHER PUBLICATIONS

Cootes, T.F. et al. The Use of Active Shape Models for Locating Structures in Medical Images. Image & Vision Computing, vol. 12, No. 6, Jul. 1994, pp. 355-366.

(Continued)

*Primary Examiner* — Christopher A Flory

(57) ABSTRACT

A parametric model representing a portion of a heart is constructed using a statistical prior of the shape from a dataset of other instances of the portion. Using a mapping electrode, electrical data is acquired in a plurality of locations in the portion of the heart of a subject. The parametric model is fitted to the electrical data and the statistical prior to produce an isosurface of the portion of the heart and a reconstruction of its shape.

22 Claims, 10 Drawing Sheets

(56) References Cited

U.S. PATENT DOCUMENTS

| | | | |
|---|---|---|---|
| 7,450,746 B2 | 11/2008 | Yang | |
| 7,536,218 B2 | 5/2009 | Govari | |
| 7,747,047 B2 | 6/2010 | Okerlund | |
| 7,756,576 B2 | 7/2010 | Levin | |
| 7,783,091 B2 | 8/2010 | Rinck | |
| 8,010,175 B2 | 8/2011 | O'Donnell | |
| 8,320,711 B2* | 11/2012 | Altmann et al. | 382/294 |
| 8,388,547 B2* | 3/2013 | Revishvili | A61B 5/04011 600/508 |
| 8,568,406 B2* | 10/2013 | Harlev et al. | 606/41 |
| 8,788,212 B2* | 7/2014 | Boyden et al. | 702/19 |
| 8,948,853 B2* | 2/2015 | Harlev et al. | 600/509 |
| 9,014,793 B2* | 4/2015 | Harlev | A61B 5/0422 600/509 |
| 9,131,869 B2* | 9/2015 | Harlev | A61B 5/0538 |
| 9,171,377 B2* | 10/2015 | Kabus | G06T 3/0081 |
| 9,277,872 B2* | 3/2016 | Harlev | A61B 5/7475 |
| 9,289,148 B2* | 3/2016 | Harlev | A61B 5/7475 |
| 2003/0013958 A1* | 1/2003 | Govari | A61B 5/0422 600/437 |
| 2003/0093004 A1* | 5/2003 | Sosa et al. | 600/544 |
| 2003/0160786 A1 | 8/2003 | Johnson | |
| 2003/0236466 A1* | 12/2003 | Tarjan | A61B 5/0408 600/508 |
| 2004/0082870 A1* | 4/2004 | Rudy et al. | 600/509 |
| 2004/0097805 A1* | 5/2004 | Verard | A61B 1/00071 600/428 |
| 2004/0097806 A1* | 5/2004 | Hunter | A61B 1/00071 600/434 |
| 2005/0058321 A1* | 3/2005 | Buehler | G06K 9/00771 382/103 |
| 2005/0107834 A1* | 5/2005 | Freeman et al. | 607/5 |
| 2005/0147325 A1* | 7/2005 | Chen | G06K 9/6212 382/294 |
| 2005/0197587 A1* | 9/2005 | Rudy et al. | 600/509 |
| 2006/0058693 A1* | 3/2006 | Beatty et al. | 600/508 |
| 2006/0084970 A1* | 4/2006 | Beatty et al. | 606/41 |
| 2006/0084972 A1* | 4/2006 | Beatty et al. | 606/41 |
| 2006/0110071 A1* | 5/2006 | Ong | G06K 9/6206 382/294 |
| 2007/0232949 A1* | 10/2007 | Saksena | A61B 5/044 600/515 |
| 2008/0009758 A1* | 1/2008 | Voth | 600/523 |
| 2008/0025638 A1* | 1/2008 | Chen | G06T 7/0034 382/284 |
| 2009/0177089 A1* | 7/2009 | Govari et al. | 600/453 |
| 2009/0297001 A1* | 12/2009 | Markowitz | A61B 5/053 382/128 |
| 2010/0022873 A1* | 1/2010 | Hunter | A61B 1/00071 600/424 |
| 2010/0113959 A1* | 5/2010 | Pascual-Leone et al. | 600/544 |
| 2010/0179421 A1* | 7/2010 | Tupin | A61B 5/026 600/426 |
| 2010/0191124 A1* | 7/2010 | Prokoski | A61B 5/0064 600/473 |
| 2010/0259263 A1* | 10/2010 | Holland | A61B 5/055 324/310 |
| 2010/0261994 A1* | 10/2010 | Davalos et al. | 600/411 |
| 2010/0274123 A1* | 10/2010 | Voth | 600/424 |
| 2010/0293512 A1* | 11/2010 | Buck | G06F 17/5045 716/132 |
| 2011/0096964 A1 | 4/2011 | Zheng | |
| 2011/0116715 A1* | 5/2011 | Wang | G06K 9/00469 382/177 |
| 2011/0144510 A1* | 6/2011 | Ryu | A61B 5/042 600/509 |
| 2011/0251505 A1* | 10/2011 | Narayan | A61B 5/0422 600/515 |
| 2012/0059249 A1* | 3/2012 | Verard | A61B 1/00071 600/424 |
| 2012/0065481 A1* | 3/2012 | Hunter | A61B 1/00071 600/301 |
| 2012/0316421 A1* | 12/2012 | Kumar | A61B 1/00009 600/407 |
| 2013/0006131 A1* | 1/2013 | Narayan | A61B 5/042 600/508 |
| 2013/0072790 A1* | 3/2013 | Ludwig | A61B 6/52 600/425 |
| 2013/0108117 A1* | 5/2013 | Kabus | G06T 3/0081 382/107 |
| 2013/0131753 A1* | 5/2013 | Simon et al. | 607/40 |
| 2013/0184792 A1* | 7/2013 | Simon | A61N 1/36025 607/115 |
| 2014/0114204 A1* | 4/2014 | Narayan | A61B 5/0422 600/518 |
| 2014/0213922 A1* | 7/2014 | Narayan | A61B 5/0422 600/515 |
| 2014/0235996 A1* | 8/2014 | Kim et al. | 600/411 |
| 2014/0257438 A1* | 9/2014 | Simon | A61N 1/0456 607/72 |
| 2014/0279304 A1* | 9/2014 | Lall | G06Q 40/12 705/30 |
| 2014/0296842 A1* | 10/2014 | Mansi et al. | 606/34 |
| 2014/0364721 A1* | 12/2014 | Lee | A61B 5/055 600/411 |
| 2014/0371613 A1* | 12/2014 | Narayan | A61B 5/0422 600/515 |
| 2014/0371807 A1* | 12/2014 | Ghosh et al. | 607/28 |
| 2014/0371808 A1* | 12/2014 | Ghosh | A61B 5/7282 607/28 |
| 2015/0173715 A1* | 6/2015 | Raghavan et al. | A61B 8/46 |
| 2015/0289807 A1* | 10/2015 | Narayan | A61B 5/0422 600/508 |
| 2016/0095531 A1* | 4/2016 | Narayan | A61B 5/0422 600/512 |

OTHER PUBLICATIONS

Karim, R. et al. Automatic Extraction of the Left Atrial Anatomy From MR for Atrial Fibrillation Ablation. ISBI'09 Proceedings of the Sixth IEEE international conference on Symposium on Biomedical Imaging: From Nano to Macro, pp. 502-505.

Kent, J.T. The Fisher-Bingham Distribution on the Sphere. J.R. Statist. Soc. B (1982), 44, No. 1, pp. 71-80.

Zahedi, "Delta Function Approximations in Level Set Methods by Distance Function Extension", J of Computation Physics 229 (2010) 2199-2219.

Ben Abdallah, A., et al., Chapter 9: "Shape Analysis of Left Ventricle Using Invariant 3-D Spherical Harmonics Shape Descriptors", 3rd International Conference on Geometric Modeling & Imaging, GMAI, pp. 53-58, XP031288343, (2008).

Chiang, P., et al., Progressive Surface Reconstruction for Heart Mapping Procedure, Computer Aided Design, vol. 44, No. 4, pp. 289-299 XP028450900 (2012).

Frangi, A., et al., "Three-Dimensional Modeling for Functional Analysis of Cardiac Images: A Review", IEEE Transactions on Medical Imaging, vol. 20, No. 1, pp. 225 XP001003250 (2001).

Garcia-Barnes, J., et al. "Endowing Canonical Geometries to Cardiac Structures", Statistical Atlases and Computational Models of the Heart, pp. 124-133, XP019152560, (2010).

Shen, L., et al., Large-Scale Modeling of Parametric Surfaces Using Spherical Harmonics, Third International Symposium on 3D Data Processing, Visualization, and Transmission, pp. 294-301 XP055174526 (2006).

Woo, J., et al. "Multi-modal Data Integration for Computer-Aided Ablation of Atrial Fibrillation", Journal of Biomedicine and Biotechnology, pp. 1-8, XP055174523, (2008).

European Search Report dated Mar. 31, 2015 for Application No. EP14176409.

\* cited by examiner

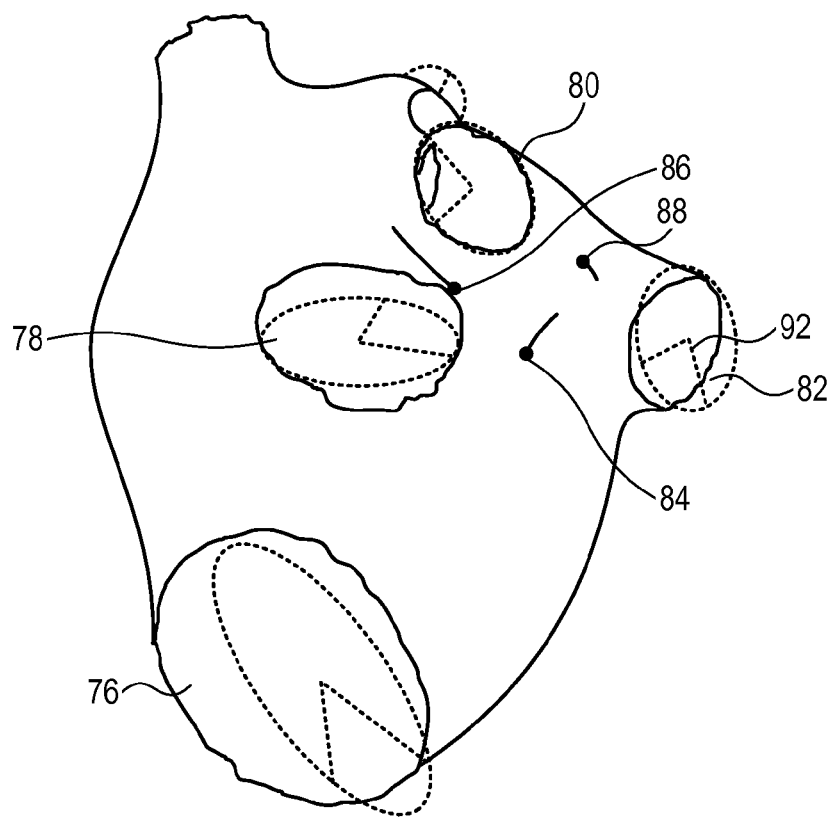
FIG. 9
FIG. 10
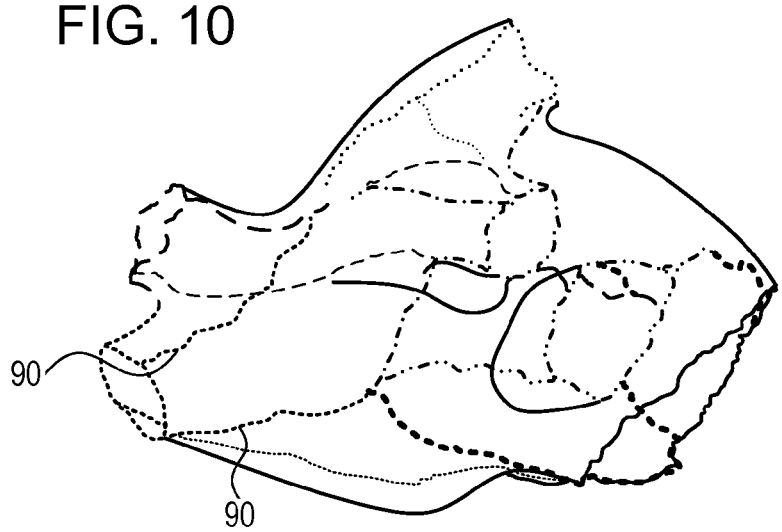

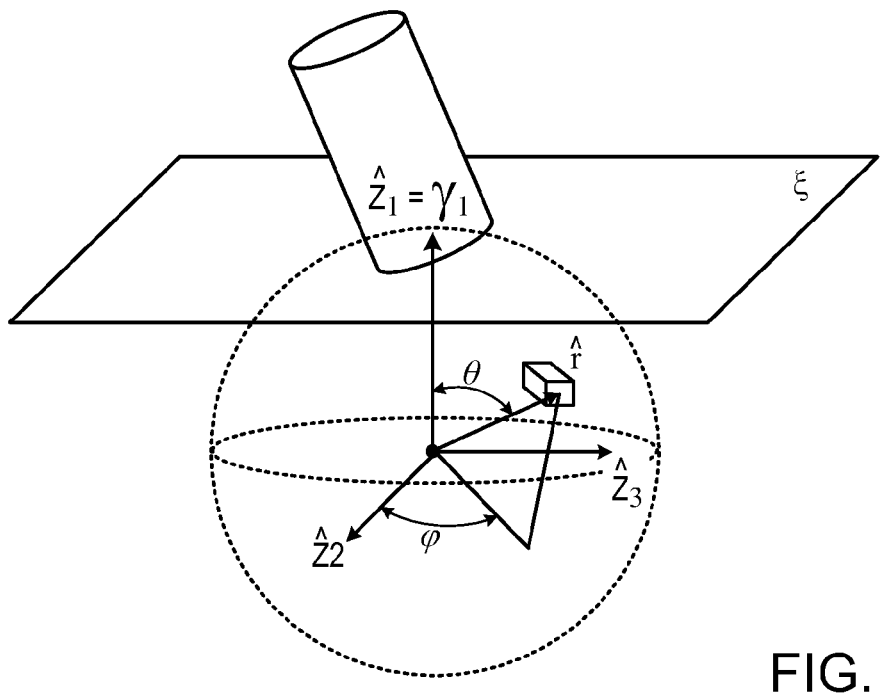
FIG. 17
FIG. 18
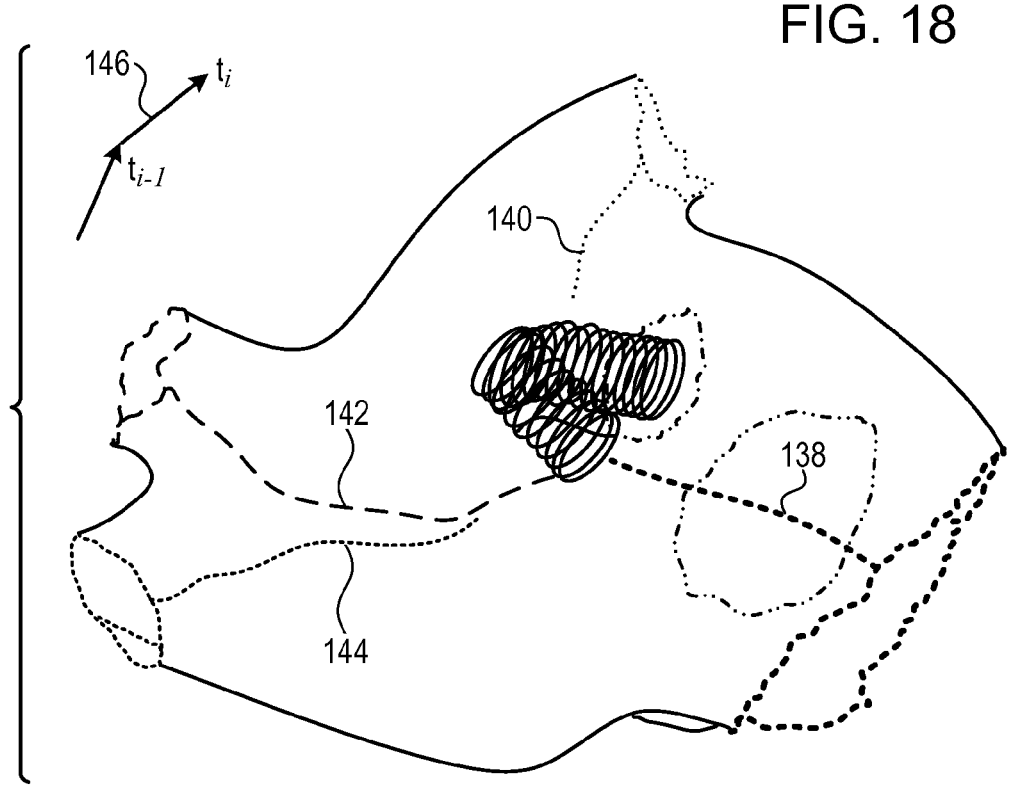

MODEL BASED RECONSTRUCTION OF THE HEART FROM SPARSE SAMPLES

CROSS-REFERENCE TO RELATED APPLICATIONS

This application claims the benefit of U.S. Provisional Application No. 61/844,024, filed 9 Jul. 2013, which is herein incorporated by reference.

BACKGROUND OF THE INVENTION

1. Field of the Invention

This invention relates to medical imaging. More particularly, this invention relates to improvements in imaging a three-dimensional structure, such as the atria of a heart.

2. Description of the Related Art

The meanings of certain acronyms and abbreviations used herein are given in Table 1.

TABLE 1

| Acronyms and Abbreviations | |
|---|---|
| FAM | Fast Anatomical Mapping |
| PV | Pulmonary Vein |
| CT | Computed Tomography |
| 3D | 3-dimensional |

Medical catheterizations are routinely carried out today. For example, in cases of cardiac arrhythmias, such as atrial fibrillation, which occur when regions of cardiac tissue abnormally conduct electric signals to adjacent tissue, thereby disrupting the normal cardiac cycle and causing asynchronous rhythm. Procedures for treating arrhythmia include surgically disrupting the origin of the signals causing the arrhythmia, as well as disrupting the conducting pathway for such signals. By selectively ablating cardiac tissue by application of energy, e.g., radiofrequency energy via a catheter, it is sometimes possible to cease or modify the propagation of unwanted electrical signals from one portion of the heart to another. The ablation process destroys the unwanted electrical pathways by formation of non-conducting lesions.

The left atrium is a complicated three-dimensional structure, the walls of which have dimensions, which differ from person to person, although all left atria have the same underlying shape. The left atrium can be divided into a number of substructures, such as the pulmonary vein, the mitral or bicuspid valve and the septum, which are conceptually easy to identify. The sub-structures also typically differ from person to person, but as for the overall left atrium, each substructure has the same underlying shape. In addition, a given substructure has the same relationship to the other substructures of the heart, regardless of the individual differences in shapes of the substructures.

SUMMARY OF THE INVENTION

There is provided according to embodiments of the invention a method, which is carried out by defining a parametric model representing a shape of a portion of a heart, and constructing a statistical prior of the shape from a dataset of other instances of the portion. The method is further carried out by inserting a probe into a living subject urging a mapping electrode of the probe into contacting relationships with tissue in a plurality of locations in the portion of the heart of the subject, acquiring electrical data from the respective locations, fitting the parametric model to the electrical data and statistical prior to produce an isosurface of the portion of the heart of the subject, and reconstructing the shape of the portion of the heart of the subject, wherein at least one of the above steps is implemented in computer hardware or computer software embodied in a nontransitory computer-readable storage medium.

According to another aspect of the method, the parametric model has internal coordinates, and defining a parametric model includes representing the shape as a field function that is defined at points within a bounding domain, and transforming the points to the internal coordinates.

In a further aspect of the method, computing the parametric model comprises computing boundary conditions on the value and the radial derivatives of the field function, In yet another aspect of the method, computing the parametric model comprises extending a solution of a Laplace equation by addition of new powers and new coefficients.

According to one aspect of the method, the bounding domain includes a unit sphere.

According to a further aspect of the method, transforming the points includes applying a skewing transformation.

According to one aspect of the method, transforming the points includes applying a spherical projection transformation.

According to a further aspect of the method, transforming the points includes applying a stretching transformation.

According to yet another aspect of the method, the transformed points correspond to tubes and ellipsoids in the parametric model, and the field function includes a tube field formula and an ellipsoid field formula, wherein fitting the parametric model includes applying the tube field formula and the ellipsoid field formula to the tubes and ellipsoids, respectively.

According to still another aspect of the method, fitting the parametric model also includes applying a blending operator to the tubes and ellipsoids.

According to an additional aspect of the method, constructing a statistical prior includes preparing segmented data meshes from cardiac computed tomographic scans.

According to another aspect of the method, fitting the parametric model includes computing anatomic features from the data meshes.

According to one aspect of the method, the anatomic features comprise at least one of a tube centerline, tube orientation, tube area, tube ellipse extent, and a ridge point.

According to a further aspect of the method, fitting the parametric model includes computing correlation coefficients among different ones of the anatomic features, According to yet another aspect of the method, relating the electrical data to the fitted parametric model includes minimizing an objective function that describes an estimated error of the parametric model with respect to the electrical data, According to still another aspect of the method, minimizing an objective function includes imposing constraints from the statistical prior on the objective function.

According to an additional aspect of the method, the objective function includes a cost function.

According to another aspect of the method, minimizing an objective function is performed by assigning respective weights to parameters of the parametric model, and iterating the objective function by varying the respective weights in respective iterations of the objective function according to an optimization schedule.

According to yet another aspect of the method, minimizing an objective function includes computing derivatives of the objective function with respect to parameters of the parametric model.

According to one aspect of the method, fitting the parametric model is performed by model component based weighting.

According to still another aspect of the method, fitting the parametric model is performed by curvature weighting.

According to an additional aspect of the method, fitting the parametric model is performed by skeleton-based fitting.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein:

FIG. 9 is a surface illustrating a phase in construction of a left atrial mesh, in accordance with an embodiment of the invention;

FIG. 10 illustrates a sparse collection of points together with a ground truth atrium surface in accordance with an embodiment of the invention;

FIG. 17 is a diagram showing definitions and angles and vectors for Lambert projection calculations, in accordance with an embodiment of the invention; and FIG. 18 is a diagram illustrating a procedure of data representation of an inflated skeleton, in accordance with an embodiment of the invention.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

System Overview

Figure 1:
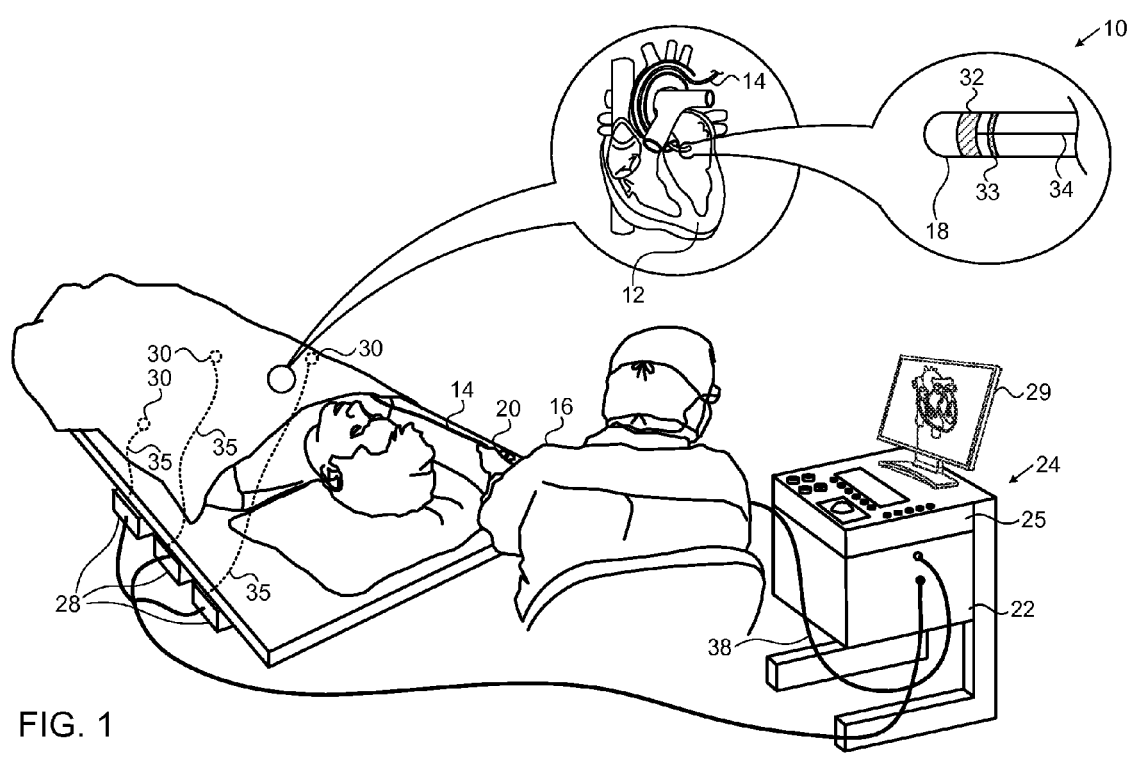
FIG. 1 is a pictorial illustration of a system for performing medical procedures in accordance with a disclosed embodiment of the invention.

Turning now to the drawings, reference is initially made to FIG. 1, which is a pictorial illustration of a system 10 for performing exemplary catheterization procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall at an ablation target site. Electrical activation maps, anatomic positional information, i.e., of the distal portion of the catheter, and other functional images may then be prepared using a processor 22 located in a console 24, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765, which is capable of producing electroanatomic maps of the heart as required. This system may be modified by those skilled in the art to embody the principles of the invention described herein for reconstruction of a structure such as the left atrium using modeling techniques as described in further detail herein.

Areas determined to be abnormal, for example by evaluation of the electrical activation maps, can be ablated by application of thermal energy, e.g., by passage of radiofrequency electrical current from a radiofrequency (RF) generator 40 through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a positioning processor 22, located in the console 24.

Ablation energy and electrical signals can be conveyed to and from the heart 12 through the catheter tip and an ablation electrode 32 located at or near the distal tip 18 via cable 34 to the console 24. Pacing signals and other control signals may be also conveyed from the console 24 through the cable 34 and the ablation electrode 32 to the heart 12. Sensing electrodes 33, also connected to the console 24 are disposed between the ablation electrode 32 and the cable 34.

Wire connections 35 link the console 24 with body surface electrodes 30 and other components of a positioning sub-system. The electrode 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near each of the electrode 32.

The console 24 typically contains one or more ablation power generators 25. The catheter 14 may be adapted to conduct ablative energy to the heart using radiofrequency energy. Such methods are disclosed in commonly assigned U.S. Pat. Nos. 6,814,733, 6,997,924, and 7,156,816, which are herein incorporated by reference.

The positioning processor 22 is an element of a positioning subsystem in the system 10 that measures location and orientation coordinates of the catheter 14. In one embodiment, the positioning subsystem comprises a magnetic position tracking arrangement that determines the position and orientation of the catheter 14 by generating magnetic fields in a predefined working volume and sensing these fields at the catheter, using field-generating coils 28. The positioning subsystem may employ impedance measurement, as taught, for example in U.S. Pat. No. 7,756,576, which is hereby incorporated by reference, and in the above-noted U.S. Pat. No. 7,536,218, As noted above, the catheter 14 is coupled to the console 24, which enables the operator 16 to observe and regulate the functions of the catheter 14. The processor 22 is typically a computer with appropriate signal processing circuits. The processor 22 is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received via cable 38 and used by the console 24 and the positioning system in order to compute the position and orientation of the catheter 14 and to analyze the electrical signals from the electrodes, and to generate desired electroanatomic maps.

The system 10 may include an electrocardiogram (ECG) monitor, coupled to receive signals from one or more body surface electrodes.

Left Atrial Reconstruction

The description that follows relates to the left atrium. This is by way of example and not of limitation. The principles of the invention are applicable to other chambers of the heart, vascular structures, and indeed, to hollow organs throughout the body. A processor in the console 24 may be suitably programmed to perform the functions described below. The programs may accept input of the above-mentioned ECG signals and other electroanatomic data that are processed by the same or other processors (not shown) in the console 24, for example, in order to reconstruct gated images.

Embodiments of the present invention reconstruct a basic underlying shape by relating measured data of a subject to respective stored model[s] of the shape and/or substructures of a hollow compartment in the body, e.g., the left atrium of the heart. In the case of the left atrium, using the model[s], it becomes possible to evaluate substructures that are difficult or impossible to visualize with cardiac catheters. The models describe different 3-dimensional shapes of the left atrium and its substructures. The models may be prepared from images acquired from any imaging system known in the art, such as intracardiac echocardiography (ICE) imaging, electroanatomic imaging, e.g., CARTO imaging, as well as by computerized tomography (CT) imaging, magnetic resonance imaging, or manual ultrasound scanning. Shape models 42 may be defined in several ways, e.g., mesh based, point based, graph based, implicit field based, and they may be based on the assumption that the heart chambers are tubes, i.e., blood vessels. In one approach, Laplace's equation or modified version thereof, considered for a fluid dynamic system in the blood vessels, can be applied to describe the desired shape. The use of Laplace's equation is exemplary. Other approaches to describing and fitting the shapes may be used, as shown in the following sections. Shape model[s] may be further constrained or re-parameterized based on statistical analysis (for example PCA) of the images database and/or models thereof.

Figure 2:
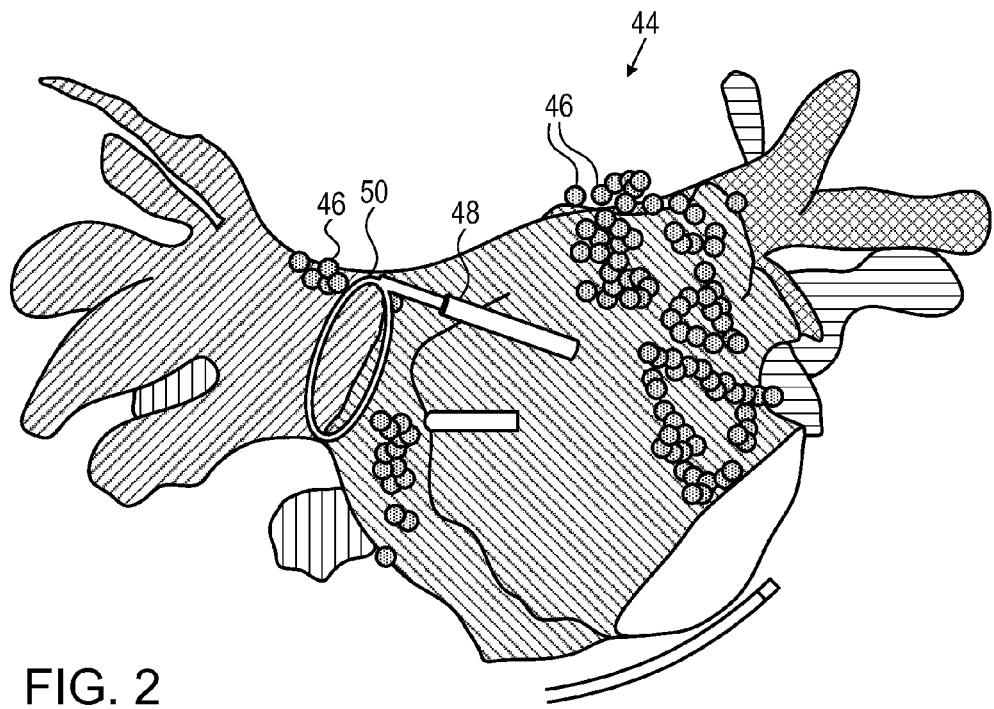
FIG. 2 is a pictorial illustration of a fast anatomical mapping procedure.

Reference is now made to FIG. 2, which is a pictorial illustration of a fast anatomical mapping procedure, which is used in accordance with an embodiment of the invention. Using a model fitting procedure, a detailed image of the left atrium of a subject may be reconstructed by fitting relatively sparse data, typically acquired during a catheterization of the left atrium, so as to arrive at a final best shape. Sparse data may be acquired by ultrasound or fluoroscopic imaging of a chamber 44 of a heart. Alternatively, sparse data 46 may be acquired by fast anatomical mapping (FAM) as shown in FIG. 2. The data 46 describe locations reported by a location sensor on the catheter, as known in the art. For example, sparse data may be acquired using the FAM functions of the CARTO 3 System cooperatively with a mapping catheter such as the Navistar® Thermocool® catheter, both available from Biosense Webster, Inc., 3333 Diamond Canyon Road, Diamond Bar, Calif. 91765. Typically, the sparse data are associated with coordinates in a 3-dimensional space, based on anatomic landmarks or fiducial marks, using location information provided by location sensors 48 on a catheter 50 as shown in FIG. 2.

Figure 3:
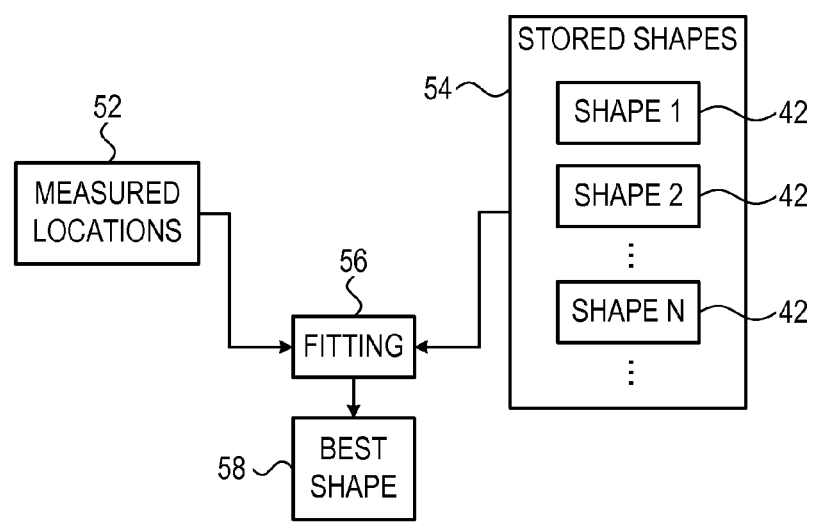
FIG. 3 is a block diagram of illustrating the fitting of measuredwhich may be used in accordance with an embodiment of the invention;locations in the heart with shape models, in accordance with an embodiment of the invention.

During a model fitting procedure, some, possibly few, and possibly high noise, measured locations of the wall of a patient's left atrium are compared with the stored shape model[s], and with the known relationships between the substructures, in a fitting procedure. Reference is now made to FIG. 3, which is a block diagram of illustrating the fitting of measured locations in the heart with shape models, in accordance with an embodiment of the invention. As shown in FIG. 3, during a catheterization, measured locations of the wall of a patient's left atrium are obtained in block 52. The measured locations are compared with shape model[s] 42 stored in a database 54, and with the known relationships between the substructures, applied to a fitting procedure in block 56. Typically, the fitting procedure applies changes to the stored shape[s], while maintaining their relationships, in order to generate a best shape 58 that is suited to the measured locations. The types and extents of the changes applied may be predetermined, and are typically based on measured available shapes as well as on physical characteristics, such as the elasticity of the substructures.

In embodiments of the invention, a parametric model is fitted to the data by minimizing an objective function, subject to a set of constraints. The approach, in general terms is as follows;

Define a parametric model representing the atrium shape;

Construct a statistical prior on the shape's features, their interrelationships, and/or shape model parameters, by statistical analysis of a dataset of ground truth left atria shapes; and Develop a model fitting procedure, that optimizes shape fit to the data, subject to constraints, with respect to the model parameters.

Realizations of the shape model, statistical prior, and model fitting procedure are described in the following sections.

First Embodiment

In this embodiment, the atrium shape is represented as the isosurface of a field function, defined at all points within a bounding domain. Each point is transformed into the internal coordinate systems of the model, by applying a series of coordinate transformations such as those described below. The contribution of each anatomical part is then computed on the transformed coordinates. The final field function is computed by blending the contributions of the anatomical parts. The coordinate transformations and field formulae of one realization of this embodiment are described in detail below, Coordinate Transformations.

Bounding Sphere Transformation.

A point t, given in the patient coordinate system, is transformed to a domain bounded by the unit sphere, by applying transformation $T_{bounds}$.

$$x_{skewed} = T_{bounds}(t)$$

In one embodiment, an affine transformation is used. The transformation parameters are chosen such that all transformed points of interest are inside the unit sphere, $\|x_{skewed}\| < 1$.

Skewing Transformation.

Figure 4:
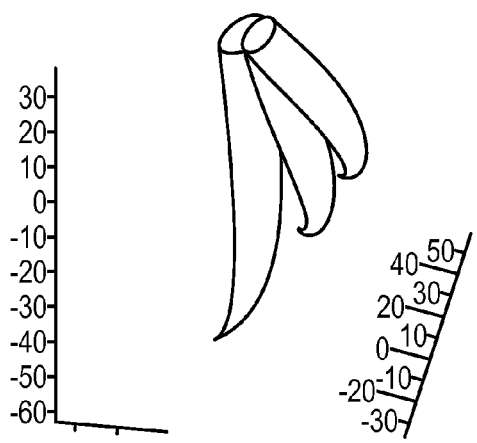
FIG. 4 is a diagram illustrating the effect of a skewing transformation on a tube-like structure, in accordance with an embodiment of the invention.

For each anatomical part j, a skewing center $x_{0,skew}^j$ is defined. A coordinate transformation is then applied, such that the origin is transformed to $x_{0,skew}^j$. In one embodiment, the transformation is defined as:

$$x_{skewed} = x^j + (1 - r_j)x_{0,skew}^j,$$

where $r_j = \|x^j\|$. This transformation may be inverted to compute coordinate vector $x^j$ given coordinate vector $x_{skewed}$. Reference is now made to FIG. 4, which is a diagram showing the effect of various parameters of the skewing transformation on a tube-like structure, in accordance with an embodiment of the invention.

Spherical Projection Transformation.

For some anatomical parts, the "unskewed" coordinates $x^1$ are projected into a flattened coordinate system by applying a spherical projection, such as the stereographic projection, such that:

$$x_{projected}^j = r_j T_{proj}\left(\frac{x^j}{r_j}\right),$$

where $T_{proj}$ is a spherical projection transformation.

Stretching Transformation.

For some anatomical parts, the projected coordinates are stretched in the z direction (perpendicular to the projection plane), by applying a stretching transformation. In one embodiment, this transformation is defined by a power transform parameterized by $\alpha_j$, such that:

$$h_j = 1 + (r_j^{\alpha_j} - 1)/\alpha_j$$

$$\xi^j = h_j T_{proj}\left(\frac{x^j}{r_j}\right).$$

Figure 5:
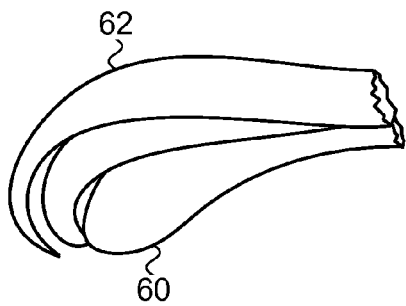
FIG. 5 is a diagram showing the effect of a stretching parameter on a tube-like structure, in accordance with an embodiment of the invention.

Reference is now made to FIG. 5, which is a diagram similar to FIG. 4 showing the effect of a stretching parameter on a tube-like structure, in accordance with an embodiment of the invention. The effect of varying the stretching parameter $\alpha_j$ on the tube-curving rate is evident in the lowermost surface 60 as compared with the uppermost surface 62. The location and orientation of the tube at its opening are constant, as are the tube target location (skewing center).

The power transform may be elaborated to a similar piecewise power transform with continuous value and derivative, with a separate $\alpha_{jk}$ parameter for each tube j and piece k.

Anatomical Part Fields.

The field contribution of each anatomical part at any given point is computed by applying a field formula to the transformed point coordinates. In one embodiment, two types of anatomical parts are used: tubes and ellipsoids.

Tube Field Formula.

Tube j is parameterized by unit vector $\mu^j$ defining the tube center, orthogonal unit vectors $\delta_{2,3}^j$ defining the principle axis directions, scalars $\lambda_{2,3}^j$ defining the axis lengths, inflation function $\eta_j(x)$, and field function $f_{tube}(\cdot)$ The field contribution $f_{tube}^j$ of the tube at a given point is defined as:

$$f_{tube}^j = f_{tubes}((\xi^j - \mu^j)^T \Sigma_j^{-1}(\xi^j - \mu^j))$$

where the cross section ellipsoid matrix $\Sigma_j^{-1}$ is given by $$\sum_j{}^{-1} = \left[\frac{\delta_2^j \delta_2^{jT}}{(\lambda_2^{j2})} + \frac{\delta_3^j \delta_3^{jT}}{(\lambda_3^{j2})}\right]/\eta_j^2(x^j)$$

In one embodiment, the inflation function $\eta_j(x)$ may be defined as a flattened power transform parameterized by $\beta_j$, such that:

$$\eta_j(x) = \frac{(r^{\beta j} - \beta_j r)}{(1 - \beta_j)},$$

where $r = \|x\|$.

Figure 6:
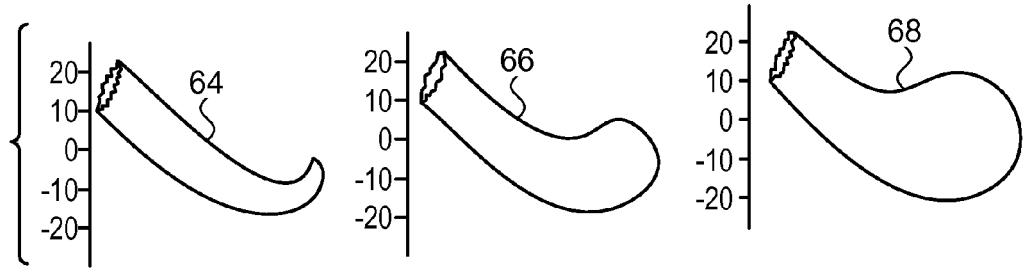
FIG. 6 is a series of three tubes illustrating the effect of an inflation parameter in accordance with an embodiment of the invention.

Reference is now made to FIG. 6, which is a series of three tubes 64, 66, 68, illustrating the effect of the inflation parameter $\beta_j$ in accordance with an embodiment of the invention. The lower right of tube 64 tapers to a point but becomes progressively bulbous in tubes 66, 68.

The inflation function may also be elaborated to a continuous smooth piecewise function with a separate $\beta_{jk}$ parameter for each tube j and piece k.

The field function $f_{tubes}(\cdot)$ may describe a standard decaying function such as a Gaussian or Lorentzian. An isosurface of $f_{tube}^j$ will describe a tube that intersects the unit sphere at $\mu^j$ with centerline direction $\delta_1^j = \delta_2^j \times \delta_3^j$ and an approximately elliptic cross section. The tube curves towards its endpoint $x_{0,skew}^j$ at a rate determined by $\alpha_j$, gradually inflating or deflating at a rate determined by the inflation function $\eta_j$.

Ellipsoid Field Formula.

Ellipsoid j is parameterized by unit vector $\mu^j$ defining its center, orthogonal unit vectors $\delta_{1,2,3}^j$ defining the principle axis directions, scalars $\sigma_{2,3}^j$ defining the axis lengths, and field function $f_{ellipsoid}(\cdot)$ The field contribution $f_{ellipsoid}^j$ of the ellipsoid at a given point is defined as:

$$f_{ellipsoid}^j = f_{ellipsoid}((x^j-\mu^j)^T \Sigma_j^{-1}(x^j-\mu^j))$$

where matrix $$\sum_j^{-1} = \sum_{1,2,3} \frac{\delta_{123}^j \delta_{123}^{jT}}{(\sigma_{123}^{j2})}.$$

Figure 7:
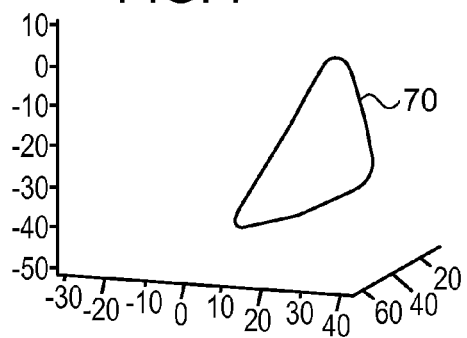
FIG. 7 is an example of a skewed ellipsoid in accordance with an embodiment of the invention.

An isosurface of $f_{ellipsoid}^j$ will describe a skewed ellipsoid centered at $\mu^j$ with skewing given by $x_{0,skew}^j$. Reference is now made to FIG. 7, which is an example of a skewed ellipsoid 70, in accordance with an embodiment of the invention.

Blending Function.

The contribution of the various anatomical points are combined by applying a blending operator. In one embodiment, this is accomplished by a pointwise linear combination of the contributions, with weight parameters $w_j$:

$$f = \sum_j w_j f^j$$

Figure 8:
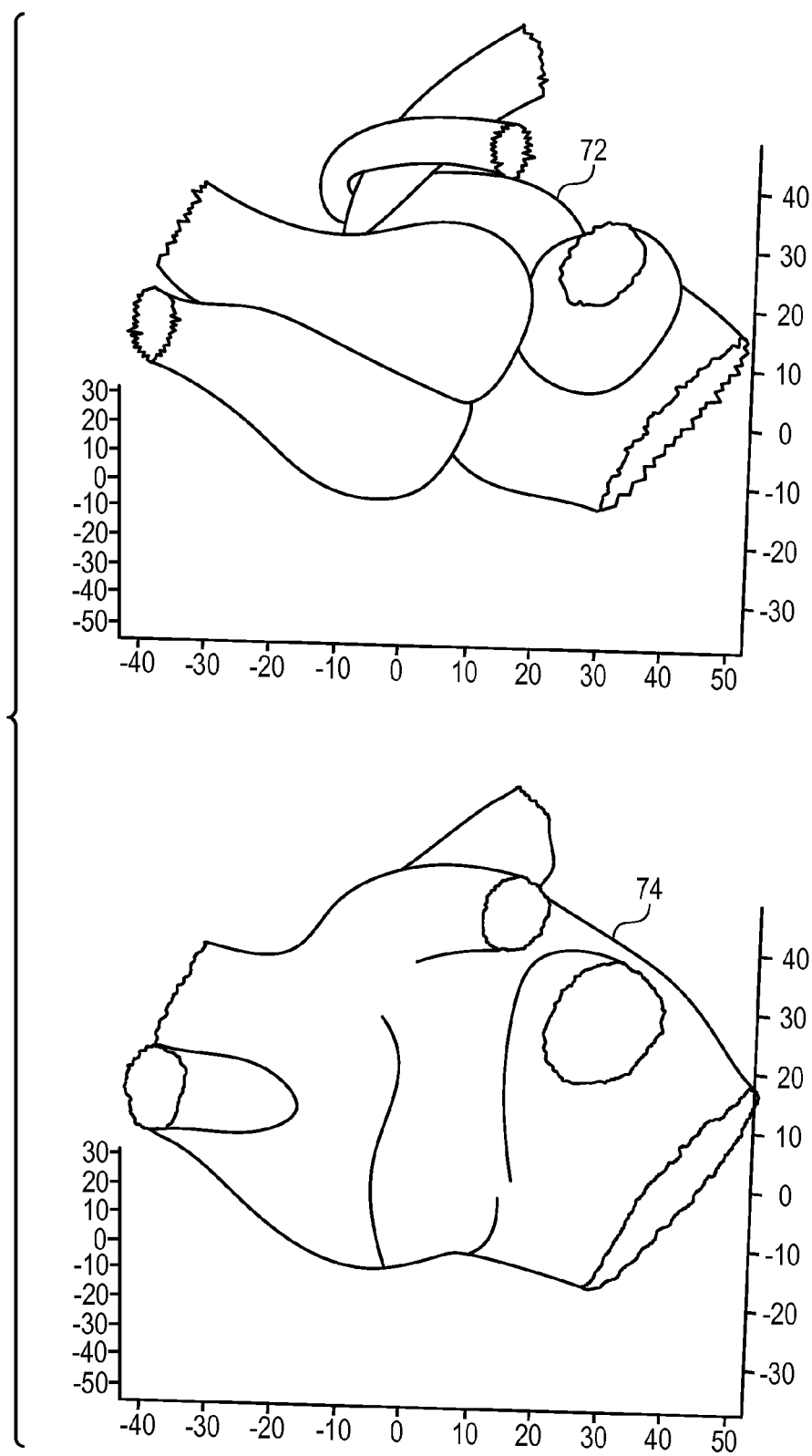
FIG. 8 is a series of two cardiac isosurfaces, illustrating the effect of a blending operator in accordance with an embodiment of the invention.

Reference is now made to FIG. 8, which is a series of two cardiac isosurfaces, illustrating the effect of a blending operator, in accordance with an embodiment of the invention. Individual parts of heart 72 in the upper part of the figure are distinct. The blending operator has been applied to yield heart 74, in which there is loss of distinctiveness, most notably of the great vessels.

Statistical Prior Model.

A statistical prior may be constructed by analyzing the anatomical features of a dataset of patients' left atria shapes. A dataset of meshes representing left atria shapes may be constructed by processing CT scans using appropriate software. In one embodiment, the shape model is fitted to each mesh in the dataset (using a model fitting procedure such as that described above), and the statistical analysis is applied to the resulting shape models and/or their parameters. Alternatively, the features may be computed directly from the data meshes.

Anatomical features such as pulmonary vein locations, orientations, and areas, may be computed from the meshes or shapes by an automated procedure. To compare the features across the dataset, the shapes are registered to a common coordinate system based on anatomical landmarks. The joint distribution of the normalized features (and/or model parameters) across the dataset may be estimated by fitting to an appropriate multivariate probability distribution. The resulting probability distribution defines a prior on the anatomical features of the left atria.

Dataset Construction.

In one embodiment, the left atria meshes are constructed from CT scans using segmentation software such as the CARTO system. The atria may be separated from the pulmonary vein trees, mitral valve, and appendage by manually cutting them such that short stumps remain connected. Reference is now made to FIG. 9, which is a surface illustrating a phase in construction of a left atrial mesh, in accordance with an embodiment of the invention. Holes 76, 78, 80, 82 resulting from the separation may be easily identified with their anatomical parts based on their location in the CT coordinates. Ridge points 84, 86, 88 are indicated by icons. The resulting meshes may then be smoothed, decimated, and corrected for topology using freely available mesh processing tool such as MeshLab, available from Sourceforge.net.

Feature Extraction.

In one embodiment, the shape model is fitted to each atrium mesh, using the procedure described below, with dense points data taken from the mesh surface. The anatomical features may then be computed from the resulting models, using the formulae described below.

Tube Centerlines.

In the $\xi^j$ coordinate system, the tube centerlines are simply straight lines. For desired height h, the tube centerline point $\xi_{ctr}^j(h)$ may therefore be computed by:

$$\xi_{ctr}^j(h) = \mu^j + (h - \mu^j \cdot \gamma_1^j) \frac{\delta_1^j}{\delta_1^j \cdot \gamma_1^j}$$

where $\gamma_1^j$ is a unit vector defining the pole of the spherical projection $T_{proj}$ for tube j.

The centerline coordinates may then be transformed to any desired coordinate system, using the coordinate transformations defined above in the section entitled Coordinate Transformations. A tube center feature may be defined by choosing height h corresponding to the tube cut locations used for the sample.

Tube Orientations.

The tube orientations are given in the $\xi^j$ coordinate system by the unit vectors $\delta_1^j$. These vectors may be transformed by multiplying them by the Jacobian matrix of the desired coordinate transformation. Orientations may be represented by orthographic projection of said unit vectors about their mean direction, yielding a 2-parameter representation of the tube direction.

Tube Areas

Tube cross section ellipse areas $A^j$ are given in any coordinate system by $A^j=\pi l_2 l_3$, where $l_2, l_3$ are given by the inverse of the eigenvaiues of matrix $\#J^{-1}\Sigma_j^{-1}J^{-1}$, where J is the Jacobian of the transformation, and # is a normalization factor computed from the tube weight and field threshold.

Tube Ellipse Extents

Tube cross section ellipses may be alternatively described by computing the projections $\hat{v}_{jk}^T \Sigma_j^{-1} \hat{v}_{jk}$, where $\hat{v}_{jk}$ denote a predefined set of unit vectors residing in the plane of the ellipse. For example, for tube j, a vector pointing towards a designated neighboring tube j' may be defined as $v_{j,neigh} = (I - \delta_1^j \delta_1^{jT})(\xi_{ctr}^{j'} - \xi_{ctr}^j)$. A set of 3 unit vectors describing the ellipse's remaining degrees of freedom may then be defined as:

$$\hat{v}_{j1} = \frac{v_{j,neigh}}{\|v_{j,neigh}\|},$$

$\hat{v}_{j2} = R(\delta_1^j, +120°)\hat{v}_{j1}$, $\hat{v}_{j3} = R(\delta_1^j, -120°)\hat{v}_{j1}$, where R(axis, angle) denotes rotation matrix around the axis at the given angle.

Ridge Points.

For two neighboring tubes j and j', an approximate midpoint line $x_{midpoint}(h)$ may be defined, by projecting the vector connecting the tubes' centerlines on to the tubes' ellipse matrices, as follows:

$$\Delta x_{ctr} \equiv x_{ctr}^{j}(h) - x_{ctr}^{j'}(h)$$

$$d['] = \sqrt{\Delta x_{ctr}^{T} \sum_{j[']}^{-1} \Delta x_{ctr}}$$

$$x_{midpoint}(h) = x_{ctr}^{j} + \frac{d'}{d+d'} \Delta x_{ctr}$$

Where centerline points $x_{ctr}^{j[']}$ and ellipse matrices $\Sigma_{j[']}^{-1}$ are transformed into the $x_{skewed}$ common coordinate system using standard point and bilinear operator transformation methods.

Reference is now made to FIG. 9, which is a surface illustrating a phase in construction of a left atrial mesh, in accordance with an embodiment of the invention. The approximate midpoint line may then be intersected with the atrium surface, by sampling some height values and detecting the point where field function reaches threshold $f = f_{thresh}$. This intersection point will occur at the ridge points 84, 86, 88, as shown in FIG. 9.

Atrium Volume.

Atrium volume may be computed by sampling the domain and summing the areas associated with all points for which $f > f_{thresh}$.

Secondary Features.

The anatomical measurements described above may be used to compute secondary features, such as:

Chord length between tube centers, e.g., left chord between left inferior PV and left superior PV;

Twist angles between the left and right chords (azimuthal and colatitude);

Tube location vector, connecting the atrium center to the tube centers, normalized to unit length, represented by orthographic projection about mean vector direction;

Angle between tube location vector and tube orientation vector;

and

Sums of tube cross-section areas.

Registration.

To compare the features across the dataset of atria, a common coordinate system is defined. In one embodiment, this origin of the coordinate system is defined as the midpoint between the left and right ridge points. A rotation and uniform scale factor may be defined such that the ridge points are transformed to coordinates (±1,0,0). An additional rotation may be defined such that the left chord is parallel to the xy plane, completing the definition of a similarity transform. The transform described here is by way of example, other variants and/or transformation families may be used to provide alternative realizations of the registration step.

Probability Distribution Estimation.

The registration transform may be applied to the anatomical features such as to normalize them to the common coordinate system. Some features, such as distance between ridge points, may be computed in the original physical coordinate system, to provide a description of the statistics of absolute atrium dimensions. The resulting feature base may be fit to a probability distribution such as multivariate normal. Standard feature selection and/or dimensionality reduction methods (such as PCA) may be used to enhance robustness of the statistical prior. The use of normal distribution is exemplary, other more advanced statistical distribution models may also be used for construction the prior.

Correlations between features may be exploited by using a joint distribution model such as multivariate normal. Our research on a dataset of atria has found significant correlations between various anatomical features, indicating their predictive power in situations where only partial information is available. Examples of these correlations are given in Table 2 (all correlations are statistically significant, after multiple comparisons correction):

TABLE 2

| Feature 1 | Feature 2 | Correlation coefficient (r) |
|---|---|---|
| Sum left PV areas | Sum right PV areas | 0.65 |
| Sum all PV areas | Valve area | 0.54 |
| Distance from appendage to valve-atrium center line segment | Valve area | 0.56 |
| Tube location unit vector (orthographic projection) | Tube orientation unit vector (orthographic projection) | 0.26-0.64 |
| Appendage center z coordinate | Distance from appendage to valve-atrium center line segment | 0.39 |
| Atrium center z coordinate | Distance from appendage to valve-atrium center line segment | 0.43 |
| Twist angle between left and right chords | Valve direction (orthographic projection y coordinate) | −0.36 |

The statistical prior term in the cost function described herein is based on the joint probability of the features, not just their marginal distributions. The correlations indicate that using the joint probability of the features during optimization should improve our ability to guess feature A (e.g., right PV areas) given information about feature B (e.g., points in the vicinity of left PV's indicating their area).

Model Fitting Procedure Embodiment.

The atrium shape model parameters are estimated by minimizing an objective function describing the estimated error of the model with respect to sparse data acquired from the patient, in conjunction with appropriate constraints. The objective and constraints functions consist of a number of terms, such as those described below. The objective function may be minimized, subject to the constraints, by standard nonlinear programming methods such as sequential quadratic programming, In one embodiment, the sparse data consists of points acquired from the atrium surface by an agreed protocol. Reference is now made to FIG. 10, which is a sparse collection of points in accordance with an embodiment of the invention, along with a ground truth atrium surface. Some of the points may describe features such as lines or rings at specific areas of the atrium, as outlined, e.g., by lines 90. Lines 90 indicate desired points in a point set that may also include general unlabeled points acquired from any part of the atrium surface.

Figure 11:
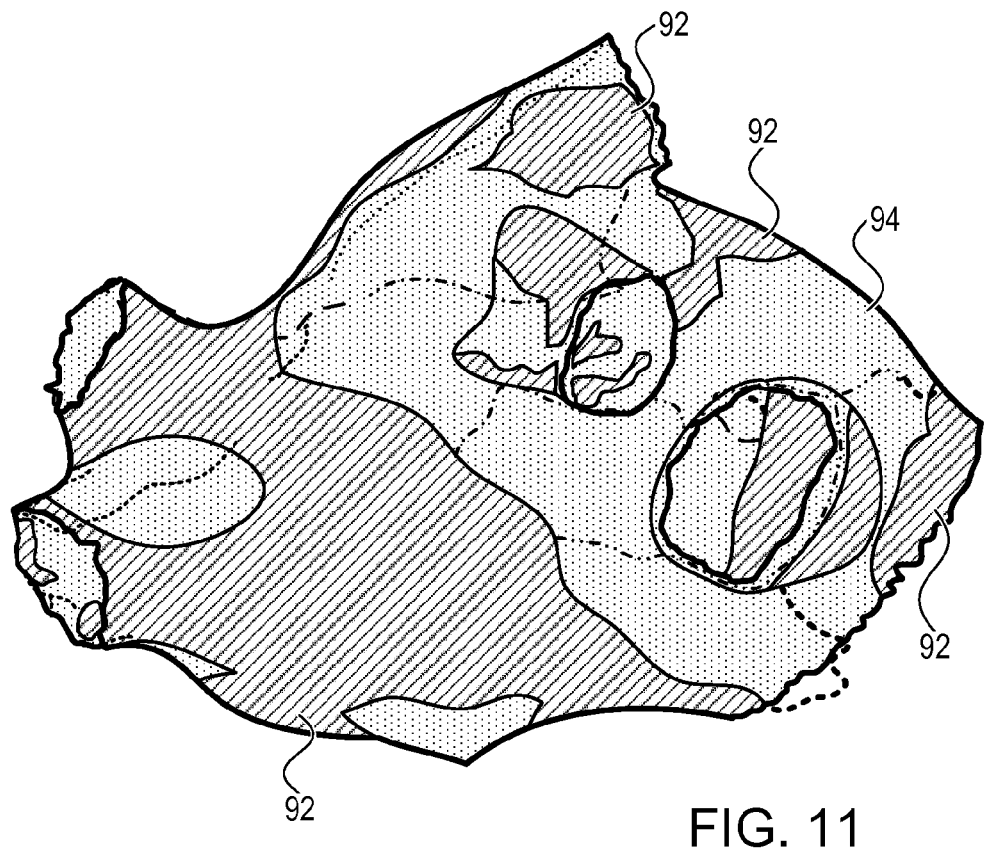
FIG. 11 is an isosurface of an atrium illustrating results of a fitting process in accordance with an embodiment of the invention.

Reference is now made to FIG. 11, which is an isosurface of an atrium illustrating results of the fitting process in accordance with an embodiment of the invention. Final model surface areas 92 are superimposed on ground truth surface 94. The ground truth surface 94 may be established by CT scans.

Approximate Distance Term.

The signed distance of a data point p from the model atrium surface may be approximated by computing:

$$d_{approx}(p) = \varphi\left(\frac{f(p) - f_{thresh}}{\|\nabla f(p)\|}\right),$$

where $f$ is the model field value at the point, $\nabla f$ is its spatial gradient, $f_{thresh}$ is a threshold parameter, and $\phi(\cdot)$ is a sigmoidal function that saturates at large values. The approximate distance may be contribute to the objective function by way of a loss function $$E_{dist} = L_{dist}(d_{approx})$$

such as square distance or a robust function such as the Huber loss function. The approximate distance may also be used as a constraint, e.g., by demanding that the data points lie outside of the model to an appropriate tolerance, $d_{approx} < d_{tot}$. The contributions of the various data points may be combined by averaging or by computing a soft maximum over the points in a given feature.

Ring Matching Term.

For ring-like point sets, typically acquired by maneuvers in tube-like structures such as pulmonary veins, a matching score may be computed to compare the ring to the corresponding tube cross section described by the model. The matching score may be based on the entire ring or on specific points defined on the ring. In one embodiment, the matching score is computed between an ellipse fitted to the data points, and the corresponding model tube cross section ellipse, using a similarity measure such as:

$$E_{ring} = L_{ring}\left[\text{trace}\left(\sum_{2d,1}^{-1} \sum_{2d,0}\right) + (\mu_{2d,1} - \mu_{2d,0})^T \sum_{2d,0}^{-1}(\mu_{2d,1} - \mu_{2d,0}) - 2 - \log\left(\frac{\det \sum_{2d,0}}{\det \sum_{2d,1}}\right)\right].$$

The subscripts 0, 1 denote data and model ellipses. The vector $\mu_{2d,*}$ denotes the ellipse center in the plane of the data points ellipse, and matrix $\Sigma_{2d,*}$ describes the ellipse in the plane. $L_{ring}(\cdot)$ is a loss function such as those described above.

Membership Term.

For data points that are known to belong to a specific anatomical part, a membership term may be computed, using the relative contributions of the model anatomical parts to the field at said point. In one embodiment, the membership score of a point p known to belong to anatomical part j is computed by:

$$E_{memb} = L_{memb}\left[\frac{w_j f^j(p)}{\sum_{j'} w_{j'} f^{j'}(p)}\right],$$

where $L_{memb}(\cdot)$ is a loss function such as those described above, Multiple points contributions may be combined e.g., by averaging or soft-max. The membership term may be incorporated in the objective function, or used as a constraint by demanding that it exceeds an appropriate threshold.

Intrinsic Model Constraints.

To ensure stability of the optimization process, a number of constraints may be applied to the model parameters and features thereof, Bounds and linear constraints may be applied to ensure the model parameters retain reasonable values. For example, a maximal ellipsoid aspect ratio of $\kappa$ may be enforced by applying the linear constraints $\sigma_i^j - \kappa \sigma_{i'}^j < 0$ for $i,i' \in \{1,2,3\}$, $i \neq i'$. Additional constraints may be applied in a nonlinear manner. For example, contiguity of the model shape may be enforced by demanding that each tube's skewing center receives a sufficient contribution from the other anatomical parts' fields, e.g., $\Sigma_{j' \neq j} w_j f^{j'}(x_{0,skew}^j) > f_{thresh}$. These constraints may be strictly enforced during the optimization, or may be applied as soft constraints by feeding the constraint into a loss function and adding the result to the full objective function.

Statistical Prior Term.

To further ensure stability, especially in cases of noisy or missing data, a statistical prior on the atrium shape model may be introduced. The prior may apply to a set of model features F such as tube centers, cross section areas, etc., as described above in the section entitled Statistical Prior Model. The prior may also apply directly to a subset of the model parameters M, after normalization to a common coordinate system. The chosen features are computed on a large database of atria. The features may be computed from ground truth atrium shapes (e.g., acquired from CT scans), and/or from the model atrium after fitting it to the samples using the procedure described above with many data points. Model parameters may similarly be taken from the model fitting results for each sample in the dataset. The prior distribution P(F, M) may assume the form of a simple parametric distribution such as multivariate normal, or a more elaborate statistical form such as a Bayesian network. The parameters of the prior distribution may be estimated from the computed features of the samples using standard procedures such as Maximum Likelihood.

The resulting prior distribution may then be used to constrain the optimization process and improve model estimation from sparse and/or noisy data. At each optimizer iteration, the required features are computed from the current estimated atrium model. The values of these features, and/or the current model parameters themselves, may be used to compute the prior probability P(F, M) for the current model. An appropriate function (e.g., log) of the prior probability may be subtracted from the objective function, or used as an optimization constraint, in order to limit the search space to models with high prior statistical likelihood, yielding pleasing results even in atrium areas with few, noisy, or no data points.

Second Embodiment

In another embodiment of the invention, a nonlinear parametric model is fitted to the data using a standard nonlinear optimization method. The approach, in general terms is as follows:
  (a) Define a parametric model of the shape with small parameter space.
  (b) Define statistical research-based constraints and/or parameter dimensionality reduction formula.
  (c) Fit to the data (optimization) using a cost function and optimization schedule, that incorporates both shape fit to data and statistical likelihood terms.

Shapes 42 may be defined in several ways, e.g., mesh based, point based, graph based.

During a model generating procedure some, possibly few, and possibly high noise, measured locations of the wall of a patient's left atrium are compared with the stored shapes, and with the known relationships between the sub-structures, in a fitting procedure. The types and extents of the changes applied may be predetermined, and are typically based on measured available shapes as well as on physical characteristics, such as the elasticity of the substructures.

The shapes described above, and the subsequent fitting of the few measured locations available, are based on assuming the heart chambers are blood vessels or tubes. In one realization, the solution of Laplace's equation may be generalized to describe an implicit field function that matches the shapes and orientations of the desired blood vessels. Reconstruction using the FAM technique is possible even under conditions of low signal-to-noise ratios and when the amount of data is very limited. As shown in FIG. 3, during a catheterization, measured locations of the wall of a patient's left atrium are obtained in block 52. The measured locations are compared with the shape models 42 using the database 54, and with the known relationships between the substructures, applied to a fitting procedure in block 56. Typically the fitting procedure applies changes to the stored shapes, while maintaining the relationships, in order to generate the best shape 58. The types and extents of the changes applied may be predetermined, and are typically based on measured available shapes as well as on physical characteristics, such as the elasticity of the substructures.

In an embodiment of the invention, a procedure for left atrial reconstruction from sparse data employs an implicit surface of a field function defined in a 3-dimensional volume. Boundary conditions are tube locations, profile and directions. The data used for the model are patient-specific meshes of atria, generated from an imaging modality, e.g., CT scans. However the meshes are also combined for the purpose of building a statistical model and reducing the dimensionality of the parameter space.

Parameters in the left atrial model have intuitive, natural meanings:

Pulmonary veins (PV's), valve, and appendage tube locations;

Axes of PV and other tubes.

PV field & directionality influence weights.

Ridge depth.

Overall volume (threshold).

Amount of "inflation" of atrial body.

Skew of atrial center.

Bounding ellipsoid.

These parameters are described more formally below.
Boundary Conditions.

The field function is defined at all locations x within the unit ball $$\mathbb{B}^3 \equiv \{x \in \mathbb{R}^3 : \|x\| \leq 1\}.$$

Its boundary conditions are therefore defined at all locations $\hat{x}$ on the surface of the unit sphere $$\mathbb{S}^2 \equiv \{\hat{x}W \in \mathbb{R}^3 : \|\hat{x}\| = 1\}.$$

Figure 12:
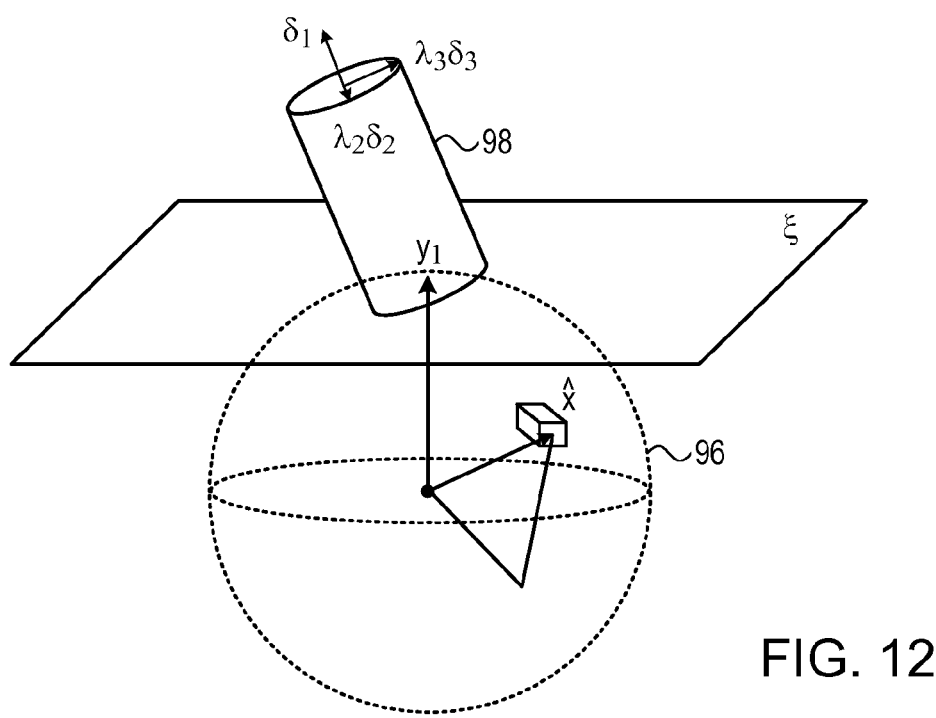
FIG. 12 is a schematic diagram illustrating aspects of a field function, in accordance with an embodiment of the invention.

Reference is now made to FIG. 12, which is a schematic diagram illustrating aspects of a field function, in accordance with an embodiment of the invention. Each tube entering the atrium (PV's, valve, and appendage), here represented by a sphere 96 contributes to the boundary conditions for the field function and for its first radial derivative. Each tube is modeled as an elliptic cylinder 98, and is fully described by the following parameters:

$\gamma_1$ is a unit vector, defining intersection of the tube centerline with the unit sphere surface.

$\delta_2, \delta_3$ are unit vectors defining the directions of the tube's ellipse axes, $\delta_2 \perp \delta_3$.

$\lambda_2, \lambda_3$ are lengths of the tube's ellipse axes,

The tube's field function at any point $\xi$ is modeled as a unit-height Gaussian, with covariance matrix defined based on the tube's ellipse axes $$f_{tube}^{(0)}(\xi) \equiv \exp\left(-\frac{1}{2}\xi^T \Sigma^{-1} \xi\right), \text{ where}$$

$$\Sigma^{-1} \equiv \Delta \Lambda^{-2} \Delta^T \text{ and } \Delta \equiv (\delta_2, \delta_3) \text{ and } \Lambda \equiv \begin{pmatrix} \lambda_2 & 0 \\ 0 & \lambda_3 \end{pmatrix}.$$

To model the influence of the tube's field at a point $\hat{x} \in \mathbb{S}^2$ on the unit sphere, the point is mapped on to the tangent plane around point $\gamma_1$, using Lambert's equal area projection:

$$\xi \equiv \sqrt{\frac{2}{1+\gamma_1^T \hat{x}}} [I_{3\times 3} - \gamma_1 \gamma_1^T] \hat{x}$$

where $I_{3\times 3}$ is the 3×3 identity matrix.

Defining $\Delta_{\parallel} \equiv [I_{3\times 3} - \gamma_1 \gamma_1^T]\Delta$, the influence of the tube at point on the unit sphere may be written as:

$$f_{tube}^{(0)} = \exp\left(-\frac{\hat{x}^T \Delta_{\parallel} \Lambda^{-2} \Delta_{\parallel}^T \hat{x}}{1+\gamma_1^T \hat{x}}\right).$$

Influence of a Tube on Boundary Field's Radial Gradients.

Pulmonary veins may blend with the atrium body at different angles. This is represented by the tubes' centerline directions $\delta_1 \equiv \delta_2 \times \delta_3$. To give full expression to these directions in the atrium model, additional boundary conditions on the field's radial gradients are defined. The contribution of a tube to the n-th order radial gradient $f_{tube}^{(n)}$ of the boundary field is modeled as the n-th order gradient of the tube's field, with respect to (w.r.t.) the projected coordinates $\xi$, in the direction of the normal $\gamma_1$:

$$f_{tube}^{(n)}(\xi) \equiv \frac{d^n f_{tube}^{(0)}(\xi + a\gamma_1)}{d a^n}\bigg|_{a=0}$$

To compute these derivatives, the function $f_{tube}^{(n)}(\xi + a\gamma_1)$ is rearranged by completing the square:

$$f_{tube}^{(0)}(\xi + a\gamma_1) = \exp\left[-\frac{1}{2}(\xi + a\gamma_1)^T \Sigma^{-1}(\xi + a\gamma_1)\right]$$

$$= \exp\left[-\frac{1}{2}\left(Z_{\gamma_1 \gamma_1}^{1/2} a + \frac{Z_{\gamma_1 \xi}}{Z_{\gamma_1 \gamma_1}^{1/2}}\right)^2\right] \exp\left(\frac{Z_{\gamma_1 \xi}^2}{2Z_{\gamma_1 \gamma_1}}\right) f_{tube}^{(0)}(\xi)$$

where $Z_{uv} \equiv u^T \Sigma^{-1} v$.

The change of variables $b \equiv Z_{\gamma_1 \gamma_1}^{1/2} a + \frac{Z_{\gamma_1 \xi}}{Z_{\gamma_1 \gamma_1}^{1/2}}$ is applied, yielding:

$$f_{tube}^{(0)}(\xi + a\gamma_1) = e^{-\frac{b^2}{2}} e^{\frac{Z_{\gamma_1 \xi}^2}{2Z_{\gamma_1 \gamma_1}}} f_{tube}^{(0)}(\xi)$$

The n-th order derivative of the exponential term is given by the well-known formula:

$$\frac{d^n e^{-\frac{b^2}{2}}}{db^n} = (-1)^n e^{-\frac{b^2}{2}} He_n(b)$$

where $He_n(b)$ are the probabilists' Hermite polynomials.

The derivative $f_{tube}^{(n)}(\xi)$ may now be computed using:

$$\frac{d^n f_{tube}^{(0)}(\xi + a\gamma_1)}{da^n} = \frac{d^n f_{tube}^{(0)}(\xi + a\gamma_1)}{db^n} Z_{\gamma_1\gamma_1}^{n/2}$$

Substituting a=0, the full expression is now given by:

$$f_{tube}^{(n)}(\xi) = (-1)^n He_n\left(\frac{Z_{\gamma_1\xi}}{Z_{\gamma_1\gamma_1}^{1/2}}\right) Z_{\gamma_1\gamma_1}^{n/2} f_{tube}^{(0)}(\xi)$$

Note that if the tube is perpendicular to the sphere, its contribution to all gradients is zero, since:

$$\delta_1 = \gamma_1 \Rightarrow \gamma_1^T \Delta = \gamma_1^T(\delta_2,\delta_3) = 0 \Rightarrow Z_{\gamma_1\xi} = Z_{\gamma_1\gamma_1} = 0.$$

Also note that:

$$\left.\frac{df_{tube}^{(n)}(\xi + a\gamma_1)}{da}\right|_{a=0} = \ldots$$

$$= (-1)^n Z_{\gamma_1\gamma_1}^{n/2} \left[\frac{d}{da}\left(He_n\left(\frac{Z_{\gamma_1,(\xi+a\gamma_1)}}{Z_{\gamma_1\gamma_1}^{1/2}}\right)\right) + He_n\left(\frac{Z_{\gamma_1,(\xi+a\gamma_1)}}{Z_{\gamma_1\gamma_1}^{1/2}}\right) \cdot \right.$$

$$\left. (-1)^1 He_1\left(\frac{Z_{\gamma_1,(\xi+a\gamma_1)}}{Z_{\gamma_1\gamma_1}^{1/2}}\right) Z_{\gamma_1\gamma_1}^{1/2}\right]_{a=0} f_{tube}^{(0)}(\xi) = \ldots$$

$$= (-1)^n Z_{\gamma_1\gamma_1}^{n/2} \left[nHe_{n-1}\left(\frac{Z_{\gamma_1\xi}}{Z_{\gamma_1\gamma_1}^{1/2}}\right)\frac{Z_{\gamma_1\gamma_1}}{Z_{\gamma_1\gamma_1}^{1/2}} - \right.$$

$$\left.\frac{Z_{\gamma_1\xi}}{Z_{\gamma_1\gamma_1}^{1/2}} He_n\left(\frac{Z_{\gamma_1\xi}}{Z_{\gamma_1\gamma_1}^{1/2}}\right) Z_{\gamma_1\gamma_1}^{1/2}\right] f_{tube}^{(0)}(\xi) = \ldots$$

$$= (-1)^{n+1} Z_{\gamma_1\gamma_1}^{(n+1)/2} \left[-nHe_{n-1}\left(\frac{Z_{\gamma_1\xi}}{Z_{\gamma_1\gamma_1}^{1/2}}\right) + \right.$$

$$\left.\frac{Z_{\gamma_1\xi}}{Z_{\gamma_1\gamma_1}^{1/2}} He_n\left(\frac{Z_{\gamma_1\xi}}{Z_{\gamma_1\gamma_1}^{1/2}}\right)\right] f_{tube}^{(0)}(\xi) = \ldots$$

$$= (-1)^{n+1} Z_{\gamma_1\gamma_1}^{(n+1)/2} He_{n+1}\left(\frac{Z_{\gamma_1\xi}}{Z_{\gamma_1\gamma_1}^{1/2}}\right) f_{tube}^{(0)}(\xi) = \ldots$$

$$= f_{tube}^{(n+1)}(\xi + a\gamma_1)$$

as desired.

Full Boundary Conditions.

Each tube contributes to the boundary condition on the field's value via its field function and influence weight $w_j^{(0)}$.

$$\hat{f}_{S^2}^{(0)j} = w_j^{(0)} f_{tube}^{(0)j}.$$

The full boundary condition on the field's value, $\hat{f}_{S^2}^{(0)}$, is defined by summing the contributions of all tubes (indexed by j), with an added baseline value $f_0$:

$$\hat{f}_{S^2}^{(0)} = f_0 + \sum_{j=1}^{N_j} f_{S^2}^{(0)j}.$$

where $N_j$ is the number of tubes. Similarly, the boundary condition on the field's n-th order radial gradient, $\hat{f}_{S^2}^{(n)}$, is defined as a weighted sum of all the tubes' contributions:

$$f_{S^2}^{(n)j} = w_j^{(n)} f_{tube}^{(n)j}$$

$$\hat{f}_{S^2}^{(n)} = \sum_{j=1}^{N_j} f_{S^2}^{(n)j}.$$

Figure 13:
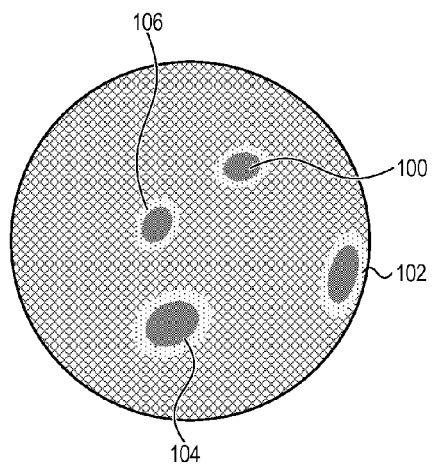
FIG. 13 is a diagram illustrating boundary conditions on a field value in accordance with an embodiment of the invention.
Figure 14:
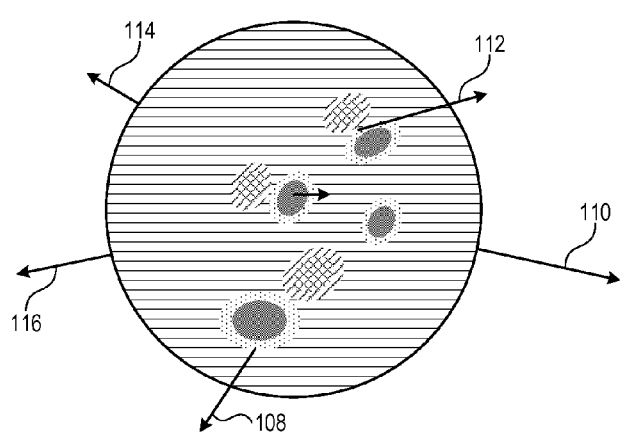
FIG. 14 is a diagram in showing boundary conditions on a field radial gradient in accordance with an embodiment of the invention.

Reference is now made to FIG. 13 and FIG. 14. FIG. 13 is a diagram illustrating boundary conditions 100, 102, 104, 106 on a field value, in accordance with an embodiment of the invention. FIG. 14 is a diagram in showing boundary conditions on a field radial gradient in accordance with an embodiment of the invention. Arrows 108, 110, 112, 114, 116 show the centerline directions of tubes (not shown) entering the sphere.

Basic Field Function Computation.

The form of the basic field function is defined as follows:

$$\hat{f}_{model}(r, \hat{x}) = \sum_{jklm} A_{jklm} r^{c_{jkl}} Y_{lm}(\hat{x})$$

where r is the distance from the origin, is a unit vector denoting the angular location of the point, and $Y_{lm}(\hat{x})$ are the real-valued spherical harmonics (SPHARM). Index $j \in \{0, \ldots, N_j\}$ covers the baseline value and the tubes' contributions. Index l runs from 0 to the maximal SPHARM degree (currently 20), and index m runs from −l to +l. The radial dependency of the field is modeled as a power law, with the power depending on l. Currently, the l-dependency is modeled as:

$$c_{jkl} = \alpha_{jk} l$$

The factors $\alpha_{jk}$ are parameters of the model that control the depth of the atrium ridges. The model extends a solution of the Laplace equation, in which $$f(r,\hat{x}) = \Sigma_{lm} A_{lm} r^l Y_{lm}(\hat{x}),$$

by addition of new powers $\alpha_{jk} l$ and new coefficients $A_{jklm}$.

The coefficients $A_{jklm}$ are computed by imposing the boundary conditions individually for each tube. The baseline value $f_0$ is imposed via the additional coefficient $A_{0000} = 4\pi Y_{00} f_0$. In general, imposing a condition on the n-th derivative (n=0, 1, . . . ) of the field contribution of tube $j \in \{0, \ldots, N_j\}$ leads to the following linear equation for each l, m:

$$\sum_k C_{jkl}^{(n)} A_{jklm} = \hat{f}_{lm}^{(n)j}$$

where:

$$\hat{f}_{lm}^{(n)j} = \int\int_{S^2} d^2\hat{x} Y_{lm}(\hat{x}) \hat{f}_{S^2}^{(n)j}$$

is the SPHARM expansion of the boundary condition on the contribution of tube j to the n-th derivative of the field function $\tilde{f}_{model}$.

The factors $C_{jkl}^{(n)}$ are given by the following recursive relationship:

$$C_{jkl}^{(0)} \equiv 1$$

$$C_{jkl}^{(n)} \equiv (c_{jkl} - n + 1) C_{jkl}^{(n-1)}.$$

All integrals over the unit sphere $\mathbb{S}^2$ may be discretized by using an appropriate uniform sphere mesh such as the icosphere.

In the current implementation, two boundary conditions are imposed: One on the field's value and one on its radial derivative, $n \in [0,1]$. Therefore, only indices $k \in [1,2]$ are used. The expressions for the coefficients are therefore given by the solution of a system of two linear equations for each l,m:

$$A_{j1lm} = \begin{cases} \dfrac{\tilde{f}_{lm}^{(1)j} - c_{j2l} \tilde{f}_{lm}^{(0)j}}{c_{j1l} - c_{j2l}}, & c_{j1l} \neq c_{j2l} \\ \tilde{f}_{lm}^{(0)j}, & c_{j1l} = c_{j2l} \end{cases}$$

$$A_{j2lm} = \tilde{f}_{lm}^{(0)j} - A_{j1lm}.$$

When $c_0(l) = c_1(l)$, the boundary condition on the derivative is ignored. For the current choice of $c_k(l) = \alpha_k(l)$, the derivative boundary condition is treated as if its mean ($0^{th}$-order component) is zero.

Inflation of the Atrium Body.

An additional inflation operation is applied to the field function after computing the coefficients:

$$\tilde{f}_{inflated}(r;\hat{x}) = r^\beta \tilde{f}_{model}(r;\hat{x})$$

Using a parameter $\beta < 0$ results in isotropic inflation of the atrium body around the origin, increasing its resemblance to a sphere. This operation was found to yield more pleasing results, as opposed to using a different l-dependency such as $c_{jk}(l) = a_{jk}l + \beta_{jk}$ when computing the solution coefficients $A_{jklm}$.

Thresholding and Isosurfacing.

A final threshold value is subtracted from the field function, giving:

$$f_{model}(r;\hat{x}) = r^\beta \tilde{f}_{model}(r;\hat{x}) - f_{thresh}$$

The threshold may be defined by its value, or by specifying the percentage of the unit ball volume the atrium should occupy, and computing the appropriate percentile of field function values within the unit ball. Varying the threshold makes the atrium thicker at all locations, as opposed to inflation, which preferentially thickens the areas closer to the origin.

The final atrium surface $f_{model}^{-1}(0)$ is defined as the zero isosurface of the model field function:

$$f_{model}^{-1}(0) \equiv \{x \in \mathbb{B}^3 : f_{model}(x) = 0\}$$

Field Function Spatial Gradient and Hessian.

The spatial gradient of the model's field function w.r.t. x is given by:

$$\nabla_x f(r;\hat{x}) = \Sigma_{jklm} A_{jklm} r^{d_{jkl}-1} V_{klm}(\hat{x}),$$

where $$V_{klm}(\hat{x}) = [d_{jkl} Y_{lm}(\hat{x}) + \Psi_{lm}(\hat{x})]$$

and $$\overline{Y}_{lm}(\hat{x}) \equiv Y_{lm}(\hat{x}) \hat{x}$$

$$\Psi_{lm}(\hat{x}) \equiv r \nabla Y_{lm}(\hat{x})$$

are the first two vector spherical harmonics.

Skew Coordinate Transformation.

Figure 15:
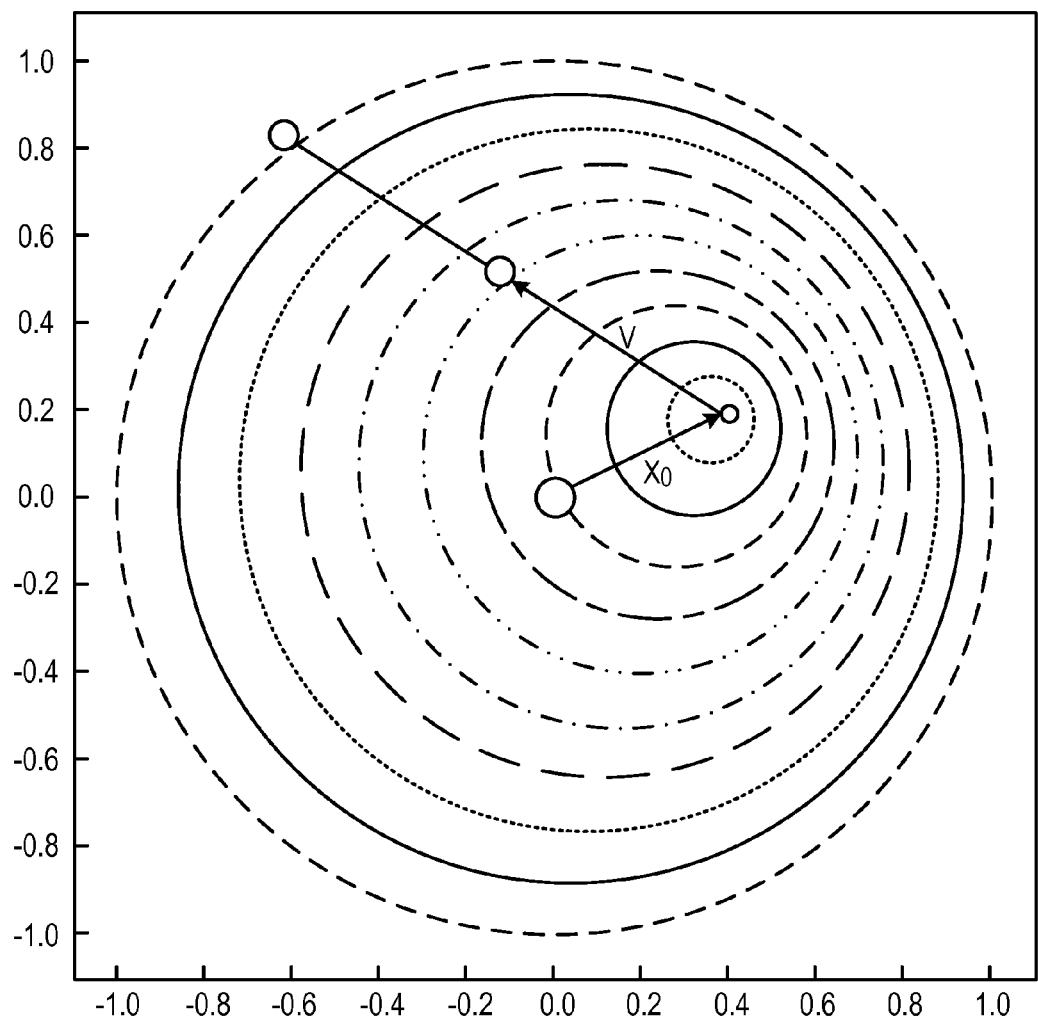
FIG. 15 is a diagram illustrating a skew coordinate transformation in accordance with an embodiment of the invention.

Reference is now made to FIG. 15, which is a diagram illustrating a skew coordinate transformation in accordance with an embodiment of the invention. The goal of the transformation is to skew the center of the atrium to point $x_0$, while keeping all points on the surface of the bounding sphere fixed at their original locations. The locations of all other points in the volume should transform smoothly. The mapping $T_{skew}: \mathbb{B}^3 \to \mathbb{B}^3$ defined for all points x in the unit ball $\mathbb{B}^3$, is represented as follows:

$$T_{skew}(x) \equiv x_0^{skew} + v(x)$$

The desired mapping is constructed such as to satisfy two conditions:

(1) All points on surface of unit sphere stay fixed:

$$T_{skew}\left(\frac{x}{\|x\|}\right) = \frac{x}{\|x\|}$$

(2) There is homogeneity of the mapping v(x) (Simple degree-1 homogeneity was found to yield the most pleasing results):

$$\forall t \in [0,1] \, v(tx) = tv(x).$$

Demanding the above two conditions yields the mapping:

$$T_{skew}(x) = x + (1 - \|x\|) x_0^{skew}.$$

In the spherical coordinate system:

$$T_{skew}(r;\hat{x}) = r\hat{x} + (1-r) x_0^{skew}.$$

The inverse transformation is given by:

$$x = v + \frac{v^T x_0^{skew} + \sqrt{(v^T x_0^{skew})^2 + \|v\|^2(1 - \|x_0^{skew}\|^2)}}{1 - \|x_0^{skew}\|^2} x_0^{skew}$$

Registration Coordinate Transformation.

Up until this point, the atrium model was defined within the bounds of the unit sphere. A linear coordinate transformation $T_{reg}: \mathbb{B}^3 \to \mathbb{R}^3$ is applied, transforming the unit sphere to an ellipsoid in the desired coordinate system. Currently, only invertible affine transformations without reflection are allowed, yielding:

$$T_{reg}(x) = Mx + t^{reg},$$

where M is a 3×3 matrix with positive determinant, and $t^{reg}$ is the translation vector. If desired, a more general transformation may be applied, e.g., a nonlinear perspective transformation.

For refined fitting optimization, discussed below, the transformation is represented by fixed parameters $M_0$ and $x_0^{reg}$ the initial transformation, and optimizable parameters $M_1$ and $x_1^{reg}$, as follows:

$$T_{reg}(x) = M_1 M_0 (x + x_0^{reg} + x_1^{reg})$$

where the fixed parameters are set to:

$$M_0 = M$$

$$x_0^{reg} = M^{-1} t^{reg}$$

and the optimizable parameters are initialized (before running the refined fitting optimization algorithm) to:

$M_1 = I$ $x_1^{reg} = 0$ leading to parameters naturally centered and scaled on the order of 1. The determinant of $M_1$ is similarly constrained to be positive.

Model Summary.

The atrium model consists of a field function and coordinate transformations, and is summarized as follows:

Field Function:
 Field:

$$f_{model}(r, \hat{x}) = \sum_{jklm} A_{jklm} r^{\alpha_{jk} l + \beta} Y_{lm}(\hat{x}) - f_{thresh}.$$

Coefficients depend on model parameters:

$A_{jklm} = A_{jklm}(\{\alpha_{jk}\}_k, \gamma_1^j, \delta_2^j, \delta_3^j, \lambda_2^j, \lambda_3^j, w_j^{(0)}, w_j^{(1)})$ Field Function Parameters:
Global Parameters:
 $\beta$=Inflation around center.
 $f_0$=Baseline (~blend with sphere)
 $f_{thresh}$=Threshold value for isosurfacing.
Per-Tube Parameters:
 $\gamma_1^j$=Tube locations on the unit sphere surface (unit vector).
 $\delta_2^j, \delta_3^j$=Tube ellipse principle axes unit vectors.
 $\lambda_2^j, \lambda_3^j$=Tube ellipse principle axes lengths.
 $w_j^{(0)}$=Field strength influence weight.
 $w_j^{(1)}$=Field derivative influence weight.
 $\alpha_{jk}$=Depth of ridges.
Constraints:
 Unit Vector $\gamma_1^{jT} \gamma_1^j = \delta_2^{jT} \delta_2^j = \delta_3^{jT} \delta_3^j = 1$ Orthogonality:

$\delta_2^{jT} \delta_3^j = 0$

Sanity:

$\alpha_k^j, \lambda_2^j, \lambda_3^j > 0, w_j^{(0)} \geq 0, w_j^{(1)} \geq 0$

Coordinate Transformations:
 Full Transformation:

$T = T_{reg} \circ T_{skew}$

Skew:

$T_{skew}(x) = x + (1 - \|x\|) x_0^{skew}$

Registration:

$T_{reg}(x) = Mx + t^{reg} = M_1 M_0 (x + x_0^{reg} + x_1^{reg})$

Coordinate Transformations Parameters:
 Parameters:
  $x_0^{skew}$=Target center after skewing (vector)
  $x_1^{reg}$=Relative translation vector
  $M_1$=Relative linear transformation matrix
 Constraints:
  Skew Bounds:

$\|x_0^{skew}\|^2 \leq 1$

No Reflection:

$det(M) > 0 \Leftrightarrow det(M_1) > 0.$

Optimization Framework.

Using the optimization framework described below, the model parameters for a known mesh may be automatically estimated, representing a CT scan of the patient's atrium. In this way the patient's atrium may be well described by specifying the above-described model parameters. In one approach, a large dataset of registered patient atria may be analyzed using the optimization framework, and their model parameters estimated. The database of parameter values may be used to construct a statistical model of the parameter values' joint distributions, The reduced dimensionality enables application of prior knowledge about atrium shapes, to enable good interpretation of the challenging, noisy, and partial FAM data without overfitting the acquired data.

Coarse Fitting.

The goal of coarse fitting is to automatically compute initial estimates for atrium parameters, given a mesh representing a patient's atrium. The initial estimates should yield an acceptable fit to the qualitative shape of the given atrium without any manual parameter tuning, and serve as initial conditions for the subsequent refined fitting process.

The input to the coarse fitting algorithm is an atrium mesh, based on computed tomographic (CT) scans corrected for topological errors and smoothed using standard methods available in MeshLab, In such a mesh, the pulmonary veins (PVs), appendage, and valve have been cut to short, tube-like stumps. The mesh contains exactly one hole for each PV, appendage and valve. The holes' centers, bounding vertices and faces are given, as well as the identity of each hole (left PV's, right PV's, appendage and valve). The mesh is given in the physical coordinate system of the original CT scan.

The bounding ellipsoid defining the registration coordinate transformation:

The center of the bounding ellipsoid $t^{reg}$ is defined simply as the centroid of the atrium mesh. The centroid is currently calculated as weighted average of its faces' centroids. Similar results are obtained when voxelizing the mesh and computing its center of mass.

Standard ellipsoid axes directions $\{\hat{\epsilon}_1, \hat{\epsilon}_2, \hat{\epsilon}_3\}$ are defined based on atrium landmarks. The first axis ("left to right" direction) is defined as the direction from the average left PV center to the average right PV center:

$$\hat{\epsilon}_1 \equiv \frac{c_{RPVs} - c_{LPVs}}{\|c_{RPVs} - c_{LPVs}\|}$$

where $c_{R[L]PVs}$ is the average of the right or left PVs' tube stumps hole centers. The third axis ("up" direction) is defined as the direction from the atrium center to the mean center of all PV's, orthogonalized to $\hat{\epsilon}_1$:

$$\hat{\epsilon}_3 \equiv -\frac{c_{PVs} - t^{reg} - [\hat{\epsilon}_1^T (c_{PVs} - t^{reg})] \hat{\epsilon}_1}{\|c_{PVs} - t^{reg} - [\hat{\epsilon}_1^T (c_{PVs} - t^{reg})] \hat{\epsilon}_1\|}.$$

The second axis direction is given by the right-hand rule by computing the cross-product:

$\hat{\epsilon}_2 = \hat{\epsilon}_3 \times \hat{\epsilon}_1.$

Bounding Ellipsoid Axes Lengths Optimization.

Given fixed directions, the bounding ellipsoids' axes should be as short as possible, while still enclosing all points in the atrium mesh. The projections of point t in the mesh on the axes' directions are defined as $\hat{t}_i \equiv \hat{\epsilon}_i^T (t - t^{reg})$ for each $i \in \{1,2,3\}$. The ellipsoid axes lengths are denoted as $\{\epsilon_i\}_{i \in \{1,2,3\}}$. The axes lengths are computed by minimizing the sum of squared axes lengths, under the constraint that all points stay within the ellipsoid. The minimization is achieved by implementing the following optimization:

$$\{\varepsilon_i^{-2}\}_{i \in \{1,2,3\}} = \underset{\{\varepsilon_i^{-2}\}}{\operatorname{argmin}} \sum_{i=1}^{3} \frac{1}{\varepsilon_i^{-2}}$$

$$\text{s.t. } \forall t \in \text{Mesh} \sum_{i=1}^{3} \varepsilon_i^{-2} t_i^2 < 1$$

and $$\forall i \in \{1, 2, 3\} \varepsilon_i^{-2} > 0.$$

In this formulation, the optimization is applied to $\epsilon_i^{-2}$. Therefore the constraints stating that all points fall within the ellipsoid become linear. The problem is then easily solvable using standard optimization algorithms.

The columns of the registration transformation matrix are now given by the axes of the bounding ellipsoid:

$$M = (\epsilon_1, \epsilon_2, \epsilon_3),$$

where $\epsilon_i \equiv \epsilon_i \hat{\epsilon}_i$.

Full bounding ellipsoid estimation:

$$\underset{\{M, x_0^{reg}\}}{\min} (\det M)$$

such that:

$$\det M > 0$$

$$\forall x \in \{x = M^{-1} t - x_0^{reg} | t \in \text{DataMesh}\} : x^T x < 1.$$

Mesh Holes Analysis.

To define the boundary conditions of the atrium model, one must specify the tubes' locations on the unit sphere, as well as their principle axes directions and lengths. All these parameters are estimated by analyzing the holes in the given atrium mesh. Only a thin "sleeve" of faces adjoining the hole's boundary is used in this analysis. All analysis is conducted on the mesh after backtransforming its points into the unit sphere coordinate system:

$$\forall t \in \text{Mesh}, x = M^{-1}(t - t^{reg})$$

Figure 16:
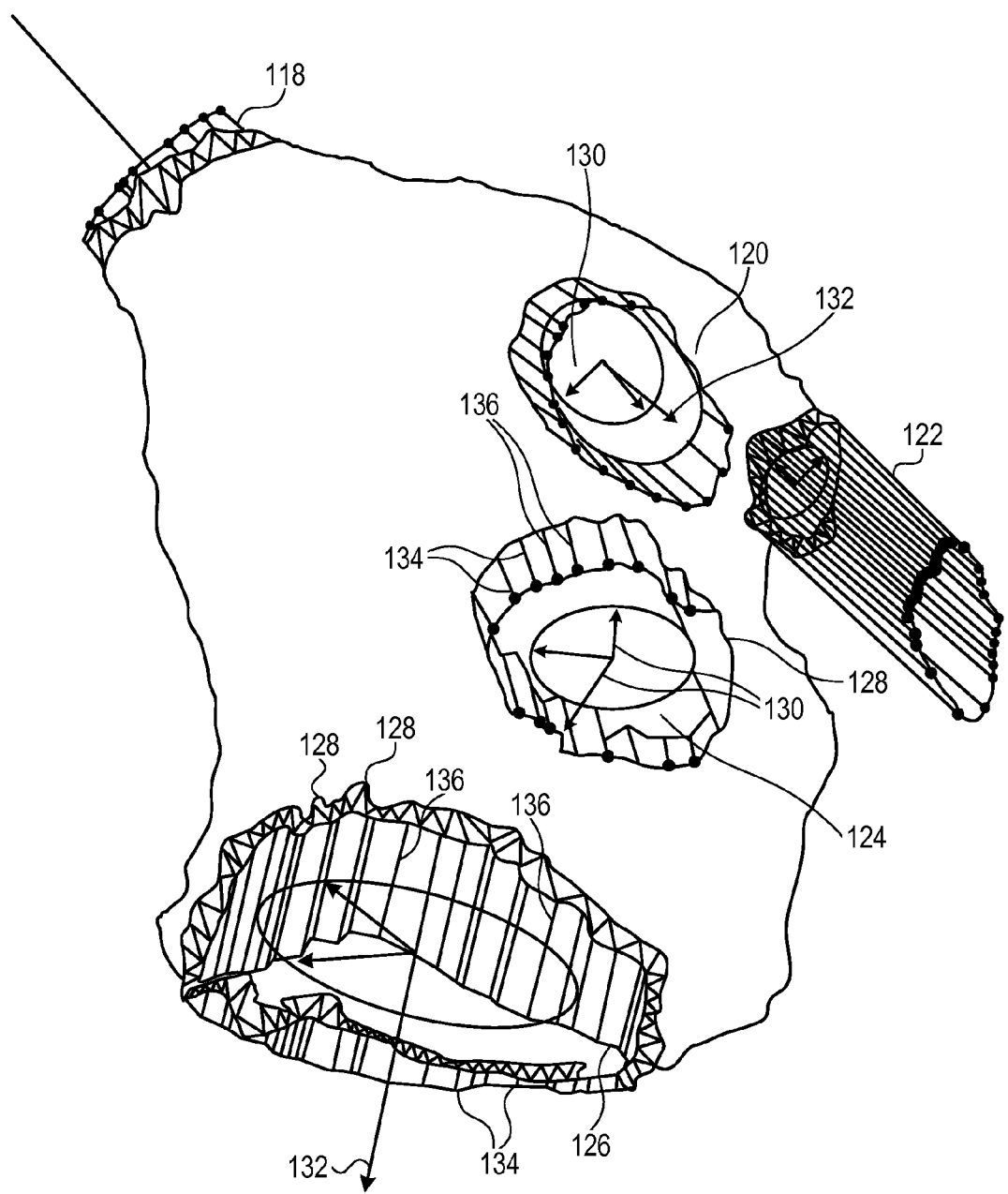
FIG. 16 is a diagram illustrating atrium mesh holes analysis, in accordance with an embodiment of the invention.

Reference is now made to FIG. 16, which is a diagram illustrating atrium mesh holes analysis, in accordance with an embodiment of the invention. Five tubes 118, 120, 122, 124, 126 are shown. As best seen in tubes 120, 124, 126, solid triangles 128 denote holes' boundary faces. Thick arrows 130 show tubes' direction vectors $\delta_1^{(j)}$. Thin arrows 132 represent axes $\epsilon_2^{(j)}, \delta_3^{(j)}$ of the tube's profile ellipse (drawn inside the hole). Dots 134 denote the holes' boundary vertices $\tilde{p}_i^{(j)}$ and their projections on to the unit sphere in the direction of $\delta_1^{(j)}$ (connected by parallel lines 136).

Tube Directions Estimation.

Continuing to refer to FIG. 16, the goal of this process is to estimate the direction of a tube, based on its hole's boundary faces (triangles 128). The normal to each boundary face is computed. The tube's direction vector $\delta_1^j$ is defined to be "as orthogonal as possible" to all of the boundary faces' normals. The projections of $\delta_1^j$ on the boundary faces' normals should therefore be minimized:

$$\delta_1^j = \underset{\delta}{\operatorname{argmin}} [\delta^T N W N^T \delta + \rho(\delta^T \delta - 1)]$$

where the columns of matrix N contain the normals to the boundary faces of hole j, the diagonal of matrix W contains their areas, and ρ is a Lagrange multiplier, introduced in order to enforce unit norm on $\delta_1^j$.

The solution of this problem is obtained by choosing $\delta_1^j$ to be the eigenvector of $NWN^T$ with the minimal eigenvalue. $\delta_1^j$ is normalized to unit norm and made to point in the outward direction.

Tube Profile Ellipse Axes Estimation.

The tube centers $\gamma_1^j$ are computed by projecting the original hole's center $\tilde{c}_j$ on to the surface of the unit sphere, in the direction of the tube's direction vector $\delta_1^j$:

$$\gamma_1^j = \tilde{c}_j + c_j \delta_1^j$$

The factor $c_j \geq 0$ is chosen such that $\gamma_1^j$ lies on the unit sphere:

$$\gamma_1^{jT} \gamma_1^j = 1$$

This condition is fulfilled by choosing:

$$c_j = -\tilde{c}_j^j \delta_1^j + \sqrt{(\tilde{c}_j^T \delta_1^j)^2 - (\delta_1^{jT} \delta_1^j (\tilde{c}_j^T \tilde{c}_j - 1))}.$$

Coarse Fitting Summary.

To summarize, the following parameters are automatically estimated in the coarse fitting process:

Registration Transformation (Bounding Ellipsoid)

$$T_{reg}(x) = Mx + t^{reg};$$

Tubes' centers $\gamma_1^j$;
Tubes' ellipses' principle axes $\delta_2^j, \delta_3^j$ and
Tubes' ellipses' axes lengths $\lambda_2^j, \lambda_3^j$.

The parameters are computed based only on the mesh holes, and its outer bounds, without using any further information about the atrium shape. Results have shown that these parameters are enough to predict the qualitative shape of a variety of patients' atria without any manual parameter tuning, using fixed values for all other parameters. The coarse fitting parameters are used as initial conditions for the subsequent refined fitting analysis.

Refined Fitting Framework.

After obtaining a coarse initial estimate for the atrium parameters, a general optimization framework is used to obtain refined estimates for all the model parameters. The mathematical basis for the optimization process consists of definition of the objective function E, and analytical computation of the objective function's derivatives $\partial_p E$ with respect to all optimizable model parameters p, given by:

$$\{p\} = \{\beta, f_0, f_{thresh}\} \cup \{\{\alpha_{jk}\}_k, \gamma_1^j, \delta_2^j, \delta_3^j, \lambda_2^j, \lambda_3^j, w_j^{(0)}, w_j^{(1)}\} \cup \{x_0^{skew}, x_1^{reg}, M_1\}.$$

The refined fitting framework is implemented in a modular fashion, allowing optimization of any subset of the model parameters, while keeping the other parameters fixed. This allows improved control over the optimization process, and understanding of the effect of the various parameters.

To ensure proper convergence, the refined fitting process is subject to appropriate constraints. The inherent model parameter constraints are given above. The surface distance error metric, ("primary candidate method") is invariant to a multiplicative constant on the field function, so at least one parameter is held fixed (e.g., valve's field strength influence weight $w_{j_{valve}}^{(0)} = 1$). Additional constraints may be employed as needed, e.g., limiting the coordinate transformation $T_{reg}$ such that the bounding ellipsoid remains at a reasonable size.

Two error metrics have been explored analytically:

Surface-to-surface error metric (Primary method): Minimize an error metric that reflects the distance between the model atrium surface and the known atrium surface, as well as their relative orientations. The distance transform of the known surface may be pre-computed for efficiency. This method is described in detail below.

Full field fitting (alternative method): Minimize the error between the full field function of the model, and a similar field function computed based on the data. The potential advantage of this method is efficiency—most computations may be done on the SPHARM coefficients $A_{klm}$, not in physical space, significantly decreasing the computational complexity. However, implementing this method requires properly revising the model field function, or proper normalization of the distance transform, to ensure that the two "field" functions exhibit comparable behavior. This method is described below.

Data Representation.

Data is given as meshes representing CT scans of patients left atria, processed in the mesh processing pipeline developed at RSIP. The PV's, appendage, and valves of these meshes are cut to short stumps. Two variations are currently implemented:

"Capped"—The tube stumps are capped automatically in the mesh processing pipeline.

"Extended": The tubes are extended in the directions computed as described in the section entitled Mesh Holes Analysis until they surpass the padded bounding cube (see below), and are subsequently re-capped.

The coordinate system of the data, typically in physical units, is denoted by coordinate vector $t \equiv T(x)$, where x is the corresponding point in the model's unit-sphere coordinate system, and T is the transformation.

The data is represented by its distance transform $D_{data}$, computed numerically in units of t on a discrete grid of voxels. Typical voxel size is $\Delta t = 0.5$ mm. The distance transform is explicitly precomputed in an initial cubeshaped region containing the initial model's bounding ellipsoid, plus some added padding. Internally, this volume is represented in t' coordinates aligned with the cube, in units of voxels, such that: $t' = [\hat{E}^T(t - t^{reg}) - t_0]/\Delta t + 1$, where the columns of $\hat{E} \equiv (\hat{\epsilon}_1, \hat{\epsilon}_2, \hat{\epsilon}_3)$ are the coordinate axes unit vectors of the initial bounding ellipsoid, $t^{reg}$ is its center, $t_0$ is the origin of the padded bounding cube in rotated coordinates, and $1 = (1, 1, 1)^T$. Note that $\hat{E}$ and $t^{reg}$ are taken from the initial bounding ellipsoid computed during coarse fitting, and are not changed during the optimization. The distance transform is given in units of t by multiplication by $\Delta t$.

The spatial gradient $\nabla_t D_{data}$ and Hessian matrix of second derivatives $\nabla_t \otimes \nabla_t D_{data}$ are similarly pre-computed within this region, using finite differences and the identities:

$$\nabla_t D_{data} = \nabla_{t'} D_{data} \hat{E}^T / \Delta t$$

$$\nabla_t \otimes \nabla_t D_{data} = \hat{E}(\nabla_{t'} \otimes \nabla_{t'} D_{data}) \hat{E}^T / \Delta t^2.$$

During optimization, these functions are sampled at the desired locations using linear interpolation with appropriate coordinate transformations.

Over the course of the optimization, the bounding ellipsoid may change. In some cases, the need may arise to extrapolate $D_{data}$, $\nabla_t D_{data}$, and $\nabla_t \otimes \nabla_t D_{data}$ beyond the initial region. To facilitate extrapolation, the clamped coordinates are defined as:

$$t'_{clamped} = \max[\max(t', 1), t'_{sz}],$$

where $t'_{sz}$ denotes the dimensions of the cube in voxels, and min, max are computed separately for each component of the vectors. For all points, the distance value is computed using:

$$D_{data}(t') D_{data}(t'_{clamped}) + \|t' - t'_{clamped}\|_1$$

where $\|\cdot\|_1$ denotes the Manhattan metric. The Manhattan metric yields smoother extrapolation fields when compared to the Euclidean metric, particularly near the transition between e.g., regions with 1 clamped coordinate and regions with 2 or more clamped coordinates, The spatial gradient is now given by:

$$\nabla_{t'} D_{data}(t') = \nabla_{t'} D_{data}(t'_{clamped}) + \text{sign}(t' - t'_{clamped})$$

Note that clamped components of $\nabla_{t'} D_{data}(t'_{clamped})$ are since $t'_{clamped}$ does not change is these directions. The sign function is applied to each component of the vector $t' - t'_{clamped}$, and is 0 for all non-clamped components.

The Hessian is given simply by:

$$\nabla_{t'} \otimes \nabla_{t'} D_{data}(t') = \nabla_{t'} \otimes \nabla_{t'} D_{data}(t'_{clamped})$$

Only non-clamped components contribute to the Hessian.

Data weights are defined as 1 on the original atrium surface, and 0 on the tubes' extensions and caps, A weighting function is defined in the entire 3D volume using the nearest neighbor on the atrium surface. This function is smoothed using a Gaussian filter with half-width equal to the maximum sampling distance $\max(\epsilon_i)\Delta x$, where $\epsilon_i$ are the initial bounding ellipsoid axis lengths, and $\Delta x$ characterizes the distance between grid points in the model's x coordinate system. The spatial gradient of the weighting function is calculated using the method described above for the distance function.

Surface-to-Surface Error Metric.

The error metric is based on the mean distance between the model and actual known atrium surfaces, as well as their relative orientations. Portions of the known atrium surface that fall outside the current model's bounding ellipsoid are penalized by assigning them a distance value.

The error metric is defined as sum of forward and backward mean distance measures, computed as a weighted average over the surfaces. All distances and surface areas are measured in the data coordinate system, $t \equiv T(x)$. Distance from model to data is based on the precomputed distance transform from the known atrium surface given in the data. Distance from data to model is approximated by normalizing the model field function by its gradient with respect to t. Near the surface, this gives an approximated distance measure, as will be shown below.

The full error metric is given by:

$$E = E_{model \to data} + E_{data \to model}$$

The model-to-data error metric is given by:

$$E_{model \to data} \equiv \frac{\mathcal{D}_{model \to data} - \phi \cdot p \cdot \mathcal{P}_{model \to data}}{\mathcal{S}_{model}}$$

where the $D_{model \to data}$ is the cumulative weighted absolute distance from the model surface to the data surface, integrated over the model surface, $P_{model \to data}$ is the cumulative weighted orientation measure, $\phi_p$ is a constant meta-parameter with units of distance, and $S_{model}$ is the total weights, integrated over the model surface.

The data-to-model error metric is given by:

$$E_{data \to model} \equiv \frac{\mathcal{D}_{data \to model}^{in} - \phi \cdot \mathcal{P}_{data \to model}^{in} + \mathcal{D}_{data \to model}^{out}}{S_{data}^{total}}$$

where $D_{data \to model}^{in}$ is the cumulative approximated absolute distance from the data to the model, integrated over the portion of the data that falls within the model's bounding ellipsoid, and $P_{data \to model}^{in}$ is the orientation measure inside the ellipsoid. For the external portion of the data surface, $D_{data \to model}^{out}$ denotes the cumulative penalty incurred, in units of distance. The total weighted surface area of the data is a precomputed constant, denoted by $S_{data}^{total}$.

The cumulative external penalty is given by:

$$\mathcal{D}_{data \to model}^{out} \equiv \iint_{t \in [T(\mathbb{B}^3)]^C \cap f_{data}^{-1}(0)} dS_t W_{data}(t) \phi_{out}(t)$$

where $f_{data}^{-1}(0)$ denotes the known atrium surface, $\phi_{out}(t)$ defines the penalty incurred by unit area on the known atrium surface that fall outside of the bounding ta's weighting function. Note that $\phi_{out}(t)$ has units of distance in the t coordinate system. The model's bounding ellipsoid is given by the transformed unit ball:

$$T(\mathbb{B}^3) = \{t = T(x) : x \in \mathbb{B}^3\}$$

and the external region is given by its complement $[T(\mathbb{B}^3)]^C$.

Currently a constant penalty $\phi_{out}(t) = \phi_{out}^{const}$ is used, so that $$D_{data \to model}^{out} = \phi_{out}^{const}(S_{data}^{total} - S_{data}^{in}),$$

where $S_{data}^{in}$ is the total surface area of the data that falls within the model's bounding ellipsoid.

Surface Functionals $D[f_{src}, f_{dst}]$, $P[f_{src}, f_{dst}]$ and $S[f_{src}]$.

The quantities $D_{model \to data}$, $P_{model \to data}$, $S_{model}$, $D_{data \to model}^{in}$, $P_{data \to model}^{in}$ and $S_{data}^{in}$ are computed using a common framework defined by three functionals, D, P, and S:

$$D_{model \to data} = D[f_{model}, f_{data}]$$

$$P_{model \to data} = P[f_{model}, f_{data}]$$

$$S_{model} = S[f_{model}]$$

$$D_{data \to model}^{in} = D[f_{data}, f_{model}]$$

$$P_{data \to model}^{in} = P[f_{data}, f_{model}]$$

$$S_{data}^{in} = S[f_{data}]$$

Surfaces are represented by the zero-value isosurface of some smooth field function $f$. The atrium model's field function $f_{model}$ is defined above in the section entitled Field Function. For the known atrium data, the signed distance transform $D_{data}$ is currently used as the data field function, $f_{data} = D_{data}$.

The estimated absolute distance from some source surface to some destination surface, integrated over the source surface within bounding domain $\mathbb{V}_t$, is given by the functional D, defined as:

$$\mathcal{D}[f_{src}, f_{dst}] \equiv \iint_{t \in T(f_{src}^{-1}(0)) \cap \mathbb{V}_t} dS_t W_{src} absdist_t[f_{dst}]$$

where the source and destination surfaces are defined via their field functions $f_{src}$ and $f_{dst}$, and the weights are given by the source weighting function $W_{src}$. The absolute distance from the destination surface in the t coordinate system, $absdist_t[f_{dst}]$, will be defined later on. This function is integrated over the source surface in the t coordinate system, $$(T(f_{src}^{-1}(0)) = \{t = T(x) : f_{src}(x) = 0\},$$

and $dS_t$ is the area element in that system. In the current setup, the bounding domain $\mathbb{V}_t$ is the model's bounding ellipsoid, given by the transformed unit ball:

$$\mathbb{V}_t = T(\mathbb{B}^3).$$

The weighted area of the source surface within the domain is given by the functional S, defined as:

$$\mathcal{S}[f_{src}] \equiv \iint_{t \in T(f_{src}^{-1}(0)) \cap \mathbb{V}_t} dS_t W_{src}$$

Currently, all measurements are sampled on a fixed spherical grid the in the model's x coordinate system (this does not affect the units of measureanent, only the numerical sampling scheme). The area element on the source isosurface $f_{src}^{-1}(0)$ transforms by a change of variables as follows:

$$dS_t = dS_x |\nabla T| \frac{\|\nabla_t f_{src}\|}{\|\nabla_x f_{src}\|}$$

where $\nabla T$ is the Jacobian matrix of transformation T, and $|\nabla|$ denotes the absolute value of its determinant. Operators $\nabla_t$ and $\nabla_x$ denote spatial gradient w.r.t. the t and the x coordinate systems, respectively.

The surface functionals are therefore given by:

$$\mathcal{D}[f_{src}, f_{dst}] = \iint_{x \in f_{src}^{-1}(0) \cap \mathbb{V}_x} dS_x |\nabla T| \frac{\|\nabla_t f_{src}\|}{\|\nabla_x f_{src}\|} W_{src} absdist_t[f_{dst}]$$

$$\mathcal{S}[f_{src}] = \iint_{x \in f_{src}^{-1}(0) \cap \mathbb{V}_x} dS_x |\nabla T| \frac{\|\nabla_t f_{src}\|}{\|\nabla_x f_{src}\|} W_{src}$$

where $\mathbb{V}_x = \mathbb{B}^3$ is the bounding domain in the x coordinate system.

In principle, $D_{model \to data}$ and $S_{model}$ could be computed using this method, by extracting the model isosurface at each iteration. However, isosurfacing is computationally intensive. In addition, computing the derivatives of these terms w.r.t. model parameters is not straightforward, since the integration region is dependent on the current model parameters. Similarly, computing $D_{data \to model}^{in}$ in this manner would require recomputing the model field function at all points on the data atrium surface at each iteration. However, model field values are most conveniently calculated on a fixed grid in spherical coordinates, i.e. in a volume.

The surface functionals are therefore reformulated as volume integrals, by applying the co-area formula. A corollary of this formula states that for any well-behaved $\phi: \mathbb{V}_x \to \mathbb{R}$, $\psi: \mathbb{V}_x \to \mathbb{R}$, $$\iint_{x \in \phi^{-1}(0) \cap \mathbb{V}_x} dS_x \frac{\psi}{\|\nabla_x \phi\|} = \iiint_{x \in \mathbb{V}_x} d^3 x \psi \delta(\phi)$$

where $\delta(\cdot)$ denotes the Dirac delta-function.

To enable application of this formula in the current setup, the x-normalized field function is defined as:

$$\phi_x^{src} \equiv \frac{f_{src}}{\|\nabla_x f_{src}\|}.$$

This function has units of x, i.e. distance in the model's coordinate system. Substituting $\phi = \phi_x^{src}$, and assuming $0 < \|\nabla_x f_{src}\| < \infty$ near the surface $f_{src}^{-1}(0)$ (i.e. the surface is a well-behaved, 2-dimensional manifold.), This assumption always holds for the data's signed distance transform. For the atrium model surface, this assumption holds everywhere but the origin, where $\phi_x^{src} \to 0$. However, the convergence is slow and $\phi$ is quite flat near the origin, so this should not cause too much biasing of the results. It follows that $\phi^{-1}(0) = f_{src}^{-1}(0)$, and the dimensionless quantity $\|\nabla_x \phi\| = 1$ on the source surface, yielding:

$$\iint_{x \in (\phi_x^{src})^{-1}(0) \cap \mathbb{V}_x} dS_x \psi = \iiint_{x \in \mathbb{V}_x} d^3 x \delta(\phi_x^{src}) \psi.$$

Substituting $$\psi = |\nabla T| \frac{\|\nabla_t f_{src}\|}{\|\nabla_x f_{src}\|} W_{src} \text{absdist}(f_{dst})$$

and $$\psi = |\nabla T| \frac{\|\nabla_t f_{src}\|}{\|\nabla_x f_{src}\|} W_{src},$$

respectively, the surface functionals are now given by:

$$\mathcal{S}[f_{src}] = \iiint_{x \in \mathbb{V}_x} d^3 x |\nabla T| \frac{\|\nabla_t f_{src}\|}{\|\nabla_x f_{src}\|} W_{src} \delta(\phi_x^{src}) \equiv \iiint_{x \in \mathbb{V}_x} dS_{src}$$

$$\mathcal{D}[f_{src}, f_{dst}] = \iiint_{x \in \mathbb{V}_x} dS_{src} \text{absdist}_t[f_{dst}].$$

In practice, the volume integrals are discretized over a spherical grid, and the Dirac $\delta$ function is approximated in the x coordinate system using:

$$\delta(x) \equiv \begin{cases} \frac{1}{2\epsilon_x}\left(1 + \cos\left(\frac{\pi x}{\epsilon_x}\right)\right), & |x| \leq \epsilon_x \\ 0, & |x| > \epsilon_x \end{cases},$$

where $\epsilon_x = 1.5 \Delta x$ is the half-width, and $\Delta X$ characterizes the typical distance between grid points. Using this $\delta$ function approximation means that the "thickness" of the surface is constant in the model's x coordinate system, averaging over approximately 3 points, as desired.

To estimate absdist$_t[f_{dst}]$, the destination field function should be converted to an approximate distance function in units of t. This is achieved by using the t-normalized field function, defined as:

$$\phi_t^{dst} \equiv \frac{f_{dst}}{\|\nabla_t f_{dst}\|}.$$

For the data, the field function is currently the signed distance transform, so $\|\nabla_t f_{data}\| = 1$, almost everywhere, yielding:

$$\tilde{\phi}_t^{data} = \phi_t^{data} = f_{data} = D_{data}$$

where $D_{data}$ is the distance from the data atrium surface, in units of the t coordinate system, sampled from the precomputed distance transform.

For the model field function, a saturation is introduced to avoid oscillations far from the atrium model surface, as follows:

$$\tilde{\phi}_t^{model} \equiv \phi_t^{max} \tanh\left(\frac{\phi_t^{model}}{\phi_t^{max}}\right).$$

The constant $\phi_t^{max}$ determines the saturation value, in units of t, and is typically set to some large distance, e.g., diagonal of bounding cube of the computed data distance transform. Near the zero isosurface, the magnitude of the spatial gradient $\|\nabla_t \tilde{\phi}_t^{model}\| = 1$, yielding an approximate distance function with the desired units.

To enforce smoothness of absdist$_t[f_{dst}]$ near the surface $f_{dist}^{-1}(0)$, a smeared approximation of the sign function is used:

$$\text{absdist}_t[f_{dst}] = \tilde{\phi}_t^{dst} \text{sign}(\phi_x^{dst})$$

where the sign function approximation with uniform thickness in the x coordinate system, is defined as sign(x)=2H(x)−1, and the Heaviside step function H(x) is represented by:

$$H(x) \equiv \begin{cases} 0, & x < -\epsilon_x \\ \frac{1}{2}\left(1 + \frac{x}{\epsilon_x} + \frac{1}{\pi}\sin\frac{\pi x}{\epsilon_x}\right), & -\epsilon_x \leq x \leq \epsilon_x \\ 1, & \epsilon_x < x \end{cases}$$

The orientation functional $P[f_{src}, f_{dst}]$ is inspired by the dipole-dipole interaction energy. The purpose of this term is to ensure that corresponding patches of the two surfaces have similar orientations. The functional is given by:

$$\mathcal{P}[f_{src}, f_{dst}] = \iiint_{x \in \mathbb{V}_x} dS_{src} \frac{\nabla_t f_{src}}{\|\nabla_t f_{src}\|} \frac{\nabla_t f_{dst}^T}{\|\nabla_t f_{dst}\|}$$

Note that the integrand is dimensionless.

Path Functional $D_{path}[t_{path}, \tilde{\phi}_t^{dst}]$.

The path functional $D_{path}[t_{path}, \tilde{\phi}_t^{dst}]$ evaluates the path integral of the optionally normalized scalar field function $\tilde{\phi}_t^{dst}$, along a path (e.g., atrium skeleton) given parametrically by $t_{path}(s_t)$, where parameter $s_t$ denotes arc length in the t coordinate system. The path integral is given by:

$$\mathcal{D}_{path}[t_{path}, \tilde{\phi}_t^{dst}] \equiv \int_0^{L_t^{path}} ds_t \tilde{\phi}_t^{dst}[T^{-1}(t_{path})]$$

where $L_t^{path}$ is the total path length in the t coordinate system.

Defining $x_{path} = T^{-1}(t_{path})$, the path integral may be represent by arc length in the x coordinate system, by substituting:

$$ds_x = \left\|\frac{dx_{path}}{ds_t}\right\| ds_t = \left\|\nabla T^{-1} \frac{dt_{path}}{ds_t}\right\| ds_t,$$

yielding:

$$\mathcal{D}_{path} \equiv \int_0^{L_x^{path}} \frac{ds_x}{\left\|\nabla T^{-1} \frac{dt_{path}}{ds_t}\right\|} \tilde{\phi}_t^{dst}(x_{path})$$

where $L_x^{path}$ is the path length in the x coordinate system.

The path integral may be converted to volume representation, as follows:

$$\mathcal{D}_{path} \equiv \iiint_{x \in \mathbb{V}_x} \frac{d^3x}{\left\|\nabla T^{-1} \frac{dt_{path}}{ds_t}(x)\right\|} \tilde{\phi}_t^{dst}(x) \int_0^{L_x^{path}} ds_x \delta_x(x - x_{path}),$$

where $\delta_x(\cdot)$ is a 3-dimensional delta function in the x coordinate system, and $$\frac{dt_{path}}{ds_t}$$

(X) represents extension of the path direction vector function $$\frac{dt_{path}}{ds_t}$$

to the full volume by nearest neighbors.

The delta function $\delta_x(\cdot)$ may be represented by a product of 3 one-dimensional delta functions in any orthogonal coordinate system. Here we pretend we are using a separable delta-function representation, such as the Gaussian approximation suggested in S. Zahedi, A. K. Tornberg, "Delta function approximations in level set methods by distance function extension", Journal of Computational Physics 229 (2010) 2199-2219. In particular, the following representation may be used:

$$\delta_x(x - x_{path}) = \delta(0)\delta(\Delta x_\|)\delta(\Delta x_\perp)$$

where $$\Delta x_\| = (x - x_{path})^T \frac{dx_{path}}{ds_x}$$

is the component of $x - x_{path}$ that lies parallel to the path, and $$\Delta x_\perp = \left\|x - x_{path} - \Delta x_\| \frac{dx_{path}}{ds_x}\right\|$$

is the component perpendicular to the path at location $s_x$. The third component is by definition zero due to the choice of local coordinate axes.

The path functional is now given by:

$$\mathcal{D}_{path} \equiv \iiint_{x \in \mathbb{V}_x} \frac{d^3x \delta(0)}{\left\|\nabla T^{-1} \frac{dt_{path}}{ds_t}\right\|} \tilde{\phi}_t^{dst} \int_0^{L_x^{path}} ds_x \delta(\Delta x_\|)\delta(\Delta x_\perp).$$

For any given x, the inner path integral sifts out the point along the path that fulfills $\Delta x_\| = 0$. For this point, $\Delta x_\perp = D_x^{path}(x)$ is simply the closest distance between x and the path. The path functional is therefore given by:

$$\mathcal{D}_{path} \equiv \iiint_{x \in \mathbb{V}_x} \frac{d^3x \delta(0)}{\left\|\nabla T^{-1} \frac{dt_{path}}{ds_t}\right\|} \delta(D_x^{path})\tilde{\phi}_t^{dst}.$$

In practice, nearest-neighbor direction vectors $$\frac{dt_{path}}{ds_t}$$

and distances $D_t^{path}$ are pre-computed in the t coordinate system, in which the path is fixed, and sampled at points $t = T(x)$. It is assumed that the coordinate transformation T has negligible effect on the identity of the nearest neighbors in the vicinity of the path. The distance $D_x^{path}$ may be approximated using $$D_x^{path} \equiv \phi_x^{path} = \frac{D_t^{path}}{\|\nabla_x D_t^{path}\|} = \frac{D_t^{path}}{\|\nabla_t D_t^{path} \nabla T\|}$$

or by $$D_x^{path} = \|\nabla_t D_t^{path} \nabla T^{-T}\| D_t^{path}.$$

Error Metric Derivatives.

For efficient and accurate optimization, the derivatives of the error metrics w.r.t. the model parameters should be calculated analytically. Note that model parameters affect both the coordinate transformation T and the field function $f_{model}$. Analytical derivative computation may be performed manually using matrix calculus, or by implementing a standard automatic differentiation algorithm for this purpose.

Data-to-Model Error Metric (Alternative Formulations).

All data-to-model error metrics may alternatively be represented as surface integrals, over the known atrium surface. The expressions for their derivatives may be simplified with the help of the divergence theorem.

Refined Fitting Framework Summary.

Error Metric.

$$E = \frac{\mathcal{D}[f_{model}, f_{data}] - \phi_{\mathcal{P}}\mathcal{P}[f_{model}, f_{data}]}{\mathcal{S}[f_{model}]} +$$

$$\frac{\mathcal{D}[f_{data}, f_{model}] - \phi_{\mathcal{P}}\mathcal{P}[f_{data}, f_{model}] + \phi_{out}^{const}(\mathcal{S}_{data}^{total} - \mathcal{S}[f_{data}])}{\mathcal{S}_{data}^{total}}$$

Surface Functionals.

$$\mathcal{S}[f_{src}] = \iiint_{x \in \mathbb{B}^3} d^3 x |\nabla T| \frac{\|\nabla_t f_{src}\|}{\|\nabla_x f_{src}\|} W_{src} \delta(\phi_x^{src}) \equiv \iiint_{x \in \mathbb{B}^3} dS_{src}$$

$$\mathcal{D}[f_{src}, f_{dst}] = \iiint_{x \in \mathbb{B}^3} dS_{src} \tilde{\phi}_t^{dst} \text{sign}(\phi_x^{dst})$$

$$\mathcal{P}[f_{src}, f_{dst}] =$$

$$\iiint_{x \in \mathbb{B}^3} dS_{src} \frac{\nabla_t f_{src}}{\|\nabla_t f_{src}\|} \frac{\nabla_t f_{dst}^T}{\|\nabla_t f_{dst}\|} \partial_p \mathcal{S}[f_{src}] = \iiint_{x \in \mathbb{B}^3} \partial_p dS_{src}$$

Normalized Field Functions $$\phi = \frac{f}{\|\nabla f\|}$$

Model Field Functions.

$$\tilde{\phi}_t^{model} \equiv \phi_t^{max} \tanh\left(\frac{\phi_t^{model}}{\phi_t^{max}}\right)$$

$$f_{model} = \sum_{jklm} A_{jklm} r^{d_{jkl}} Y_{lm}(\hat{x}) - f_{thresh}$$

Model Field Function Spatial Gradients.

$$\nabla_x D_{data} = \nabla_t D_{data} \nabla T$$

$$\partial_p (\nabla_x D_{data}) = \partial_p (\nabla_t D_{data}) \nabla T + \nabla_t D_{data} \partial_p \nabla T$$

$$\partial_p (\nabla_t D_{data}(T(x))) = [\nabla_t \otimes \nabla_t D_{datap} T]^T$$

Model Coefficients $$\sum_k C_{jkl}^{(n)} A_{jklm} = \tilde{f}_{lm}^{(n)j}$$

$$\sum_k C_{jkl}^{(n)} \partial_p A_{jklm} = \partial_p \tilde{f}_{lm}^{(n)j} - \sum_k \partial_p C_{jkl}^{(n)} A_{jklm}$$

Data Field Functions.

$$\tilde{\phi}_t^{data} = \phi_t^{data} = f_{data} = D_{data}$$

Data Field Functions Spatial Gradients.

$$\nabla_x D_{data} = \nabla_t D_{data} \nabla T$$

Lambert Equal-Area Projection.

The desired boundary condition for the field of a tube blending into the unit sphere should be shaped like a Gaussian defined on the surface of the sphere. The canonical definition for such a function is known as the Kent distribution. By using the Lambert projection, the tube field function $f_{tube}$ approximates the shape of this distribution (Kent, J. T. 1982: "The Fisher-Bingham distribution on the sphere", J. Royal. Stat. Soc., 44:71-80). Using the projection, rather than the original Kent distribution, enables calculating the field without having to explicitly compute the eigenvectors $\gamma_2$, $\gamma_3$ defined in the paper. This yields simpler expressions for the derivatives of the objective functions computed in the optimization stage.

Reference is now made to FIG. 17, which is a diagram showing definitions and angles and vectors for Lambert projection calculations, in accordance with an embodiment of the invention. The Lambert azimuthal equal-area projection is a mapping from a sphere to a disk that accurately represents area in all regions of the sphere. The disk may be considered to be positioned on the tangent plane centered around a chosen pole $\hat{z}$ on the surface of the sphere. In this scenario, a projection $\zeta$ of point $\hat{x}$ is given by (Kent, J. T. 1982):

$$\xi(\hat{x}) \equiv \left(2\sin\frac{\theta}{2}\cos\varphi\right)\hat{z}_2 + \left(2\sin\frac{\theta}{2}\sin\varphi\right)\hat{z}_3$$

where $\theta$ is the polar angle, $\phi$ is the azimuth, $\hat{z}_2, \hat{z}_3$ are orthogonal unit vectors defining the coordinate system, as shown in FIG. 17. The desired pole is located at the intersection of the PV centerline with the sphere surface, $\hat{z} = \gamma_1$. The required functions of the angles $\theta$, $\phi$, can be expressed as follows:

$$\sin\frac{\theta}{2} = \sqrt{\frac{1-\cos\theta}{2}} = \sqrt{\frac{1-\gamma_1^T \hat{x}}{2}}$$

$$\cos\varphi = \hat{z}_2^T \hat{x}_{\parallel}$$

$$\sin\varphi = \hat{z}_3^T \hat{x}_{\parallel}$$

where:

$$\hat{x}_{\parallel} \equiv \frac{\hat{x} - (\gamma_1^T \hat{x})\gamma_1}{\|\hat{x} - (\gamma_1^T \hat{x})\gamma_1\|}$$

Substituting these expressions and using orthogonality of the axes, the following expression is obtained:

$$\xi = \sqrt{\frac{2}{1+\gamma_1^T \hat{x}}} [I_{3\times 3} - \gamma_1 \gamma_1^T]\hat{x},$$

where $I_{3\times 3}$ the identity matrix. Note that this expression is independent of the choice of the axes $\hat{z}_2$, $\hat{z}_3$. As desired, near $\gamma_1$, the transformed point is approximately equal to the original point:

$$\xi = \hat{x} - \gamma_1 + O(\|\hat{x} - \gamma_1\|^2).$$

The norm $\|\xi\|$ attains its minimal value of 0 at the pole $\hat{x}=\gamma_1$, and attains its maximal value of 2 at the antipode $\hat{x}=-\gamma_1$ as can be found by taking the limit of the norm squared:

$$\|\xi\|^2 \xrightarrow{\hat{x}\to-\gamma_1} 4.$$

Alternative Refined Fitting Method—Full Field Fitting.

The advantage of this method is that optimization may be performed in the space of coefficients $A_{klm}$, rather than physical space. However special adaptations would be required to ensure that the full model and data field functions have similar behavior. For example, the model field function currently diverges to infinity at the origin, The objective function is defined as the mean squared error (MSE) between the model field function, and a field function representing the known atrium data. This is currently computed based on distance transform from the patient's atrium mesh, and sampled using the coordinate transform T as defined in the model described in the section entitled "Model Summary":

$$E = \int_0^1 r^2 dr \iint_{\mathbb{S}^2} d^2\hat{x} [f_{model}(r,\hat{x}) - f_{data}(T(r,\hat{x}))]^2$$

Using the orthogonality of spherical harmonics, and evaluating the integrals, the objective function can be formulated as a sum over the SPHARM indices l,m, rather that over the full 3D volume, enabling efficient computation. The objective function is then given by:

$$E = A_{klm} Z_{kk'lm} A_{k'lm} - 2 A_{klm} I_{klm} + \Phi_{data}^{lm}.$$

Summation is performed over all indices in the RHS, and the terms are defined as follows:

$A_{klm}$ are the coefficients as defined in the model,
Normalization factors: $Z_{kk'lm} \equiv [d_k(l)+d_{k'}(l)+3]^{-1}$.
Exponents: $d_k(l) \equiv c_k(l)+\beta$.
Data integrals: $I_{klm} \equiv \int_0^1 dr\, r^{d_k(l)+2} f_{data}^{lm}(r,T)$
Data field SPHARM expansion:

$$f_{data}^{lm}(r,T) \equiv \iint_{\mathbb{S}^2} d^2\hat{x} Y_{lm}(\hat{x}) f_{data}(T(r,\hat{x}))$$

Data power:

$$\phi_{data}^{lm} \equiv \int_0^1 dr\, r^2 [f_{data}^{lm}(r,T)]^2.$$

Omitting indices l,m, and absorbing indices k,k' into matrix-vector product notation, the objective function can be written as:

$$E = A^T Z A - 2 A^T I + \Phi_{data}$$

To perform efficient and accurate optimization, it is desirable to use analytical computation of the objective function's derivatives with respect to the model parameters. Since the atrium model is fully specified in analytical terms, the derivatives with respect to all model parameters may also be computed analytically.

Implementation Details.
Optimization Improvements.

The following section outlines procedures for incremental improvements in optimization using improved initial linear transformation estimation, data weighting integration, and skeleton-based fitting.

Improved Initial Linear Transformation.

The following procedure is run:

Optimize all transformation parameters (transformation matrix, center);

Find minimal-volume ellipsoid that includes all data points:

$$\min_{\{M, x_0^{reg}\}} (\det M)$$

such that $\det M > 0$ $\forall x \in \{x = M^{-1} t - x_0^{reg} | t \in \text{DataMesh}\} : x^T x < 1$ Two schemes for atrium model weighting may be employed: Model component based weighting Decompose the model function by its tube components:

$$f_{j_{model}} = \sum_{klm} A_{jklm} r^{d_{jkl}} Y_{lm}(\hat{x}) + w_{ball} \sum_{klm} A_{0klm} r^{d_{0kl}} Y_{lm}(\hat{x}) - f_{thresh}$$

The constant component (Ball) is added by a factor to each tube component.

Compute the Phi function for each component:

$$\phi_j = \frac{f_j}{\|\nabla f_j\|}$$

Heuristic: phi_j represents the distance from the component. The ridges are places where (transformed) products of phi_j's are high.

Phi transformation (Student-t function:

$$w(x,\mu,\sigma) = \left(1+\left(\frac{x}{\sigma}\right)^2\right)^{\frac{-(1+\mu)}{2}}$$

Selected component products:

$$w_{model} = w(\phi_{right\ superior},\mu,\sigma_{right})*w(\phi_{right\ inferior},\mu,$$
$$\sigma_{right}) + \alpha(w(\phi_{left\ superior},\mu,\sigma_{left})*w(\phi_{left\ inferior},\mu,$$
$$\sigma_{left}) + (w(\phi_{left\ superior},\mu,\sigma_{left\_s\ app})*w(\phi_{appendage},\mu,$$
$$\sigma_{left\_app}) + (w(\phi_{left\ superior},\mu,\sigma_{left\_i\ app})*w$$
$$(\phi_{appendage},\mu,\sigma_{left\_i\ app}) + (w(\phi_{left\ superior},\mu,$$
$$\sigma_{left\_s\_i\ app}) w(\phi_{left\ inferior},\mu,\sigma_{left\_s\_i\ app})*w$$
$$(\phi_{appendage},\mu,\sigma_{left\_s\_i\ app}))$$

The goal of this weighting scheme is to assign increased weight to ridge regions. However, it is not as accurate as curvature weighting (described below).

Curvature Weighting

The curvature for implicit surface in 3D is given as:

Gaussian Curvature $$K_G = \frac{\nabla F * H^*(F) * \nabla F^T}{|\nabla F|^4} = -\frac{\begin{vmatrix} H(F) & \nabla F^T \\ \nabla F & 0 \end{vmatrix}}{|\nabla F|^4}.$$

Mean Curvature $$K_M = \frac{\nabla F * H(F) * \nabla F^T - |\nabla F|^2 \text{Trace}(H)}{2|\nabla F|^3} = \frac{-\text{coeff}(\lambda)\text{in}\begin{vmatrix} H(F)-\lambda I & \nabla F^T \\ \nabla F & 0 \end{vmatrix}}{2|\nabla F|^3}.$$

This method is dependent on Hessian matrix, and can be computed either: numerically (in spherical coordinates) or analytically, Skeleton-Based Fitting.

Principles: —Start from a thin version of the model, and fit it to the data skeleton, —Gradually inflate data representation and model. Always keep model surface inside data surface, to prevent local minima.

Data Skeleton Computation.

Define atrium center as maximum of distance transform D from the data surface.

Compute optimal path from tube hole center to atrium center, using Dijkstra algorithm:

Energy function: 1/D,

Graph definition: Connect all neighboring voxels, edge weights={distance between the voxels}*(1/Dsrc 1/Ddst)/2

Skeleton-based optimization framework.

Use thin model, with fixed threshold & no "ball". The signed dislance from data skeleton to model surface may be computed as follows:

$$\mathcal{D}^{skel} = \int_{Skeleton} ds \tilde{\phi}_t^{model}(T^{-1}(t_{skel}(s)))$$

The model surface should be parallel to skeleton, and possibly to the data surface. This may be quantified using the orientation functional:

$$\mathcal{P}[f_{src}, f_{dst}] = \iiint_{x \in \mathbb{B}^3} dS_{src} \frac{\nabla_t f_{src}}{\|\nabla_t f_{src}\|} \frac{\nabla_t f_{dst}^T}{\|\nabla_t f_{dst}\|}$$

The model surface should not be outside data surface: Modify existing distance measure to penalize outside portions. Skeleton should be as far inside the model as possible, by maximizing the signed distance functional. Skeleton orientation may be constrained by incorporating the orientation functional in a cost function or nonlinear constraint function during optimization.

Data Representation—Inflated Skeleton.

Reference is now made to FIG. 18, which is a diagram illustrating a procedure of data representation of the inflated skeleton, in accordance with an embodiment of the invention.

Compute skeleton arms 138, 140, 142, 144 (Dijkstra, 1/D cost, weighted by path segment length)

Start from the hole's ellipse, scaled by a scale factor.

Each point along the skeleton arm is assigned an ellipse, by transforming the previous ellipse axes.

Transformation is defined by the change in the tangent to the skeleton arm. Referring to a set of vectors 146:

$$AXIS = t_{i-1} \times t_i$$

$$ANGLE = \cos^{-1}(t_{i-1} \cdot t_i)$$

Label the entire volume by ellipse of nearest neighbor on the skeleton,

Central blob: Define threshold as min distance from outer atrium surface, across all center point ellipses (one for each tube)·When scale factors are large, central blob is the full atrium.

Optimization Stages.

Initial thin guess—PV locations & directions based on skeleton tips Maximize skeleton depth within model (change only tube locations and directions):

$$\mathcal{D}_{skel \to model} \equiv \int_{skel} ds \phi_{model}$$

Fit model to thin inflated skeleton with thin valve. Use "full-sized" valve, (first only global and valve parameters, then all parameters).

Gradually inflate.

Optimization Constraints.

Model must stay inside the next stage's data representation. Conversely, next-stage data must stay outside the model. As noted above, the skeleton must stay inside the model.

Use "soft minima" constraint functional,

To help all model areas stay inside the boundary, add "cut-off" exponential term to cost function:

$$\mathcal{D}_{exp}[f_{src}, f_{dst}] = \iiint_{x \in \mathbb{V}_X} dS_{src} cutexp(-\tilde{\phi}_t^{dst})$$

$$cutexp(\phi) = \begin{cases} \phi_{slope}\phi_{capture}e^{\phi/\phi_{capture}} & \phi < \phi_{max} \\ \phi_{slope}e^{\phi_{max}/\phi_{capture}}(\phi_{capture} + \phi - \phi_{max}) & \phi > \phi_{max} \end{cases}$$

In alternate embodiments the following options may be implemented:

Higher derivatives boundary conditions using a general formula:

$$f_{tube}^{(n)}(\xi) = (-1)^n He_n\left(\frac{Z_{\gamma_1 \xi}}{Z_{\gamma_1 \gamma_1}^{1/2}}\right) Z_{\gamma_1 \gamma_1}^{n/2} f_{tube}^{(0)}(\xi)$$

$$Z_{uv} \equiv u^T \Sigma^{-1} v$$

$$\xi \equiv \sqrt{\frac{2}{1 \div \gamma_1^T \hat{x}}} [I_{3\times 3} - \gamma_1 \gamma_1^T] \hat{x}$$

This allows slightly sharper tube angles.

An additional weak "tube" may be added for cases with short common ostium.

Tube Constraints.
For each PV & appendage:
Weight area near the tube opening ("long-cut" of the data).
Soft-max of distance must be within tolerance.
Soft-max of orientation match must be within tolerance.
2×2 constraints per tube: (data, model)×(distance, orientation), used in all fitting stages.
Valve not constrained (treated like atrium body).

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention clamied is:

1. A method, comprising the steps of:
defining, by a computer processor, a parametric model representing a shape of a portion of a heart;
constructing, by the computer processor, a statistical prior of the shape from a dataset of other instances of the portion, the dataset including the portions of hearts from a plurality of patients, and wherein constructing the statistical prior comprises preparing segmented data meshes;
fitting, by the computer processor, the parametric model to the statistical prior, wherein fitting the parametric model comprises computing anatomic features from the data meshes and computing correlation coefficients among different ones of the anatomic features;
inserting a probe into a living subject, the probe having a mapping electrode;
urging the mapping electrode into contacting relationships with tissue in a plurality of locations in the portion of the heart of the subject;
acquiring electrical data from the respective locations;
relating the electrical data to the fitted parametric model to produce an isosurface of the portion of the heart of the subject; and
reconstructing the shape of the portion of the heart of the subject responsively to relating the electrical data.

2. The method according to claim 1, wherein the parametric model has internal coordinates, and wherein defining a parametric model comprises:
representing the shape as a field function that is defined at points within a bounding domain; and
transforming the points to the internal coordinates to define transformed points.

3. The method according to claim 2, wherein the field function has a value and radial derivatives, further comprising computing the parametric model by computing boundary conditions on the value and the radial derivatives.

4. The method according to claim 2, wherein the parametric model comprises a spherical harmonic expansion having powers and coefficients, further comprising extending a solution of the Laplace equation by addition of new powers and new coefficients.

5. The method according to claim 2, wherein the bounding domain comprises a unit sphere.

6. The method according to claim 2, wherein transforming the points comprises applying a skewing transformation.

7. The method according to claim 2, wherein transforming the points comprises applying a spherical projection transformation.

8. The method according to claim 2, wherein transforming the points comprises applying a stretching transformation.

9. The method according to claim 2 wherein the transformed points correspond to tubes and ellipsoids in the parametric model, and the field function comprises a tube field formula and an ellipsoid field formula, wherein fitting the parametric model comprises applying the tube field formula and the ellipsoid field formula to the tubes and ellipsoids, respectively.

10. The method according to claim 9, wherein fitting the parametric model further comprises applying a blending operator to the tubes and ellipsoids.

11. The method according to claim 1, wherein the anatomic features comprise at least one of a tube centerline, tube orientation, tube area, tube ellipse extent, and a ridge point.

12. The method according to claim 1, wherein relating the electrical data to the fitted parametric model comprises minimizing an objective function that describes an estimated error of the parametric model with respect to the electrical data.

13. The method according to claim 12, wherein minimizing an objective function comprises imposing constraints from the statistical prior on the objective function.

14. The method according to claim 12, wherein the objective function comprises a cost function.

15. The method according to claim 12, wherein minimizing an objective function is performed by assigning respective weights to parameters of the parametric model; and iterating the objective function by varying the respective weights in respective iterations of the objective function according to an optimization schedule.

16. The method according to claim 12, wherein minimizing an objective function comprises computing derivatives of the objective function with respect to parameters of the parametric model.

17. The method according to claim 1, wherein fitting the parametric model comprises model component based weighting.

18. The method according to claim 1, wherein fitting the parametric model comprises curvature weighting.

19. The method according to claim 1, wherein fitting the parametric model comprises skeleton-based fitting.

20. A method, comprising the steps of:
defining, by a computer processor, a parametric model representing a shape of a portion of a heart;
constructing, by the computer processor, a statistical prior of the shape from a dataset of other instances of the portion, wherein constructing the statistical prior comprises preparing segmented data meshes;
fitting, by the computer processor, the parametric model to the statistical prior by computing anatomic features from the data meshes and computing correlation coefficients among different ones of the anatomic features, wherein computing correlation coefficients comprises using a joint distribution model;
inserting a probe into a living subject, the probe having a mapping electrode;
urging the mapping electrode into contacting relationships with tissue in a plurality of locations in the portion of the heart of the subject;
acquiring electrical data from the respective locations;
relating the electrical data to the fitted parametric model to produce an isosurface of the portion of the heart of the subject; and
reconstructing the shape of the portion of the heart of the subject responsively to relating the electrical data.

21. The method according to claim 20, wherein constructing the statistical prior comprises a cost function based on a joint probability of a feature.

22. The method according to claim 21, wherein the construction of the statistical prior comprises determining a feature A based on given information of a feature B.

\* \* \* \* \*